United States Patent
Alizadeh et al.

(10) Patent No.: US 11,311,225 B2
(45) Date of Patent: Apr. 26, 2022

(54) SYSTEMS AND METHODS FOR SHIELDED AND ADJUSTABLE MEDICAL MONITORING DEVICES

(71) Applicant: General Electric Company, Schenectady, NY (US)

(72) Inventors: Azar Alizadeh, Schenectady, NY (US); Andrew A. Burns, Schenectady, NY (US); Matthew Jeremiah Misner, Delanson, NY (US); Ralf Lenigk, Schenectady, NY (US); Jeffrey Michael Ashe, Gloversville, NY (US); Obi Aghogho, Troy, NY (US); Nancy Cecelia Stoffel, Schenectady, NY (US); Juha Virtanen, Helsinki (FI); Otto Pekander, Helsinki (FI); Timo Toivanen, Helsinki (FI); Robert Santala, Helsinki (FI)

(73) Assignee: General Electric Company, Schenectady, NY (US)

( * ) Notice: Subject to any disclaimer, the term of this patent is extended or adjusted under 35 U.S.C. 154(b) by 657 days.

(21) Appl. No.: 16/027,057

(22) Filed: Jul. 3, 2018

(65) Prior Publication Data

US 2019/0015008 A1 Jan. 17, 2019

Related U.S. Application Data

(60) Provisional application No. 62/531,106, filed on Jul. 11, 2017.

(51) Int. Cl.
*A61B 5/282* (2021.01)
*A61B 5/00* (2006.01)
(Continued)

(52) U.S. Cl.
CPC ............ *A61B 5/282* (2021.01); *A61B 5/6823* (2013.01); *A61B 5/6832* (2013.01); *A61B 5/01* (2013.01);
(Continued)

(58) Field of Classification Search
CPC . A61B 5/04085; A61B 5/6832; A61B 5/6823; A61B 5/14542; A61B 5/01; A61B 5/6824; A61B 5/684; A61B 5/6828
(Continued)

(56) References Cited

U.S. PATENT DOCUMENTS 5,933,307 A * 8/1999 West .................. H01T 4/08
361/56
6,006,125 A 12/1999 Kelly et al.
(Continued)

OTHER PUBLICATIONS

Yonghee Kim, Controlled electro-spray deposition of highly conductive PEDOT:PSS films, Mar. 2012, Elsevier, vol. 98, pp. 39-45 (Year: 2012).*
(Continued)

*Primary Examiner* — Linda C Dvorak
*Assistant Examiner* — Nils A Potter

(57) ABSTRACT

A system for monitoring medical conditions includes a conformable medical monitoring device that includes a first substrate layer, which includes an electronics module, many signal traces, and at least one electrode, such that one or more of the many signal traces electrically couple the at least one electrode to the electronics module. The conformable medical monitoring device includes a second substrate layer positioned over the electronics module, the first substrate layer, or any combination thereof to insulate the electronics module, the first substrate layer, or any combination thereof. The conformable medical monitoring device also includes a third substrate layer positioned over the second substrate layer, such that the third substrate layer reduces electromag-
(Continued)

netic interference caused by a voltage pulse and includes an adjustable system coupled to the first substrate layer and that changes a position of the at least one electrode relative to the electronics module.

20 Claims, 22 Drawing Sheets

(51) Int. Cl.
*A61B 5/145* (2006.01)
*A61B 5/01* (2006.01)

(52) U.S. Cl.
CPC ........... *A61B 5/14542* (2013.01); *A61B 5/684* (2013.01); *A61B 5/6824* (2013.01); *A61B 5/6828* (2013.01)

(58) Field of Classification Search
USPC ........................................................ 600/391
See application file for complete search history.

(56) References Cited

U.S. PATENT DOCUMENTS

| | | | |
|---|---|---|---|
| 6,716,165 | B1 | 4/2004 | Flanders et al. |
| 6,751,493 | B2* | 6/2004 | Wenger .............. A61B 5/04085 600/382 |
| 8,180,425 | B2 | 5/2012 | Callahan et al. |
| 8,706,215 | B2 | 4/2014 | Kaib et al. |
| 2006/0224073 | A1 | 10/2006 | Lin et al. |
| 2008/0312522 | A1* | 12/2008 | Rowlandson ...... A61B 5/04085 600/382 |
| 2011/0288605 | A1* | 11/2011 | Kaib ...................... A61B 5/053 607/5 |
| 2013/0116520 | A1 | 5/2013 | Roham et al. |
| 2014/0066741 | A1* | 3/2014 | Peterson ............ A61B 5/04085 600/393 |
| 2014/0343392 | A1* | 11/2014 | Yang .................. A61B 5/04082 600/393 |
| 2015/0257685 | A1* | 9/2015 | Pushpala .............. A61B 5/7278 600/345 |
| 2015/0374251 | A1* | 12/2015 | Yoshioka ........... A61B 5/04011 600/386 |
| 2017/0000359 | A1 | 1/2017 | Kohli et al. |
| 2017/0019988 | A1* | 1/2017 | McGrane ............. A61B 5/0408 |
| 2017/0127961 | A1* | 5/2017 | Schmidt ............... A61B 5/0022 |
| 2017/0281925 | A1* | 10/2017 | Silver .................. A61B 5/4848 |
| 2017/0303808 | A1* | 10/2017 | Stone .................. A61B 5/6804 |
| 2018/0008158 | A1 | 1/2018 | Virtanen |
| 2018/0008160 | A1 | 1/2018 | Virtanen |
| 2018/0168458 | A1 | 6/2018 | Pekander et al. |
| 2018/0168507 | A1* | 6/2018 | Virtanen .............. A61B 5/0809 |
| 2019/0175094 | A1* | 6/2019 | Ortiz .................... A61B 5/4266 |
| 2020/0128670 | A1* | 4/2020 | Chong Rodriguez ....................... H05K 1/0272 |

OTHER PUBLICATIONS

Khadija Kanwal Khanum, Evaluation of electromagnetic interference shielding using Poly(3,4-ethylenedioxythiophene) Polystyrene sulfonate blend, 2016, IEEE (Year: 2016).*

Chung, Wan-Young, et al.; "A wireless sensor network compatible wearable u-healthcare monitoring system using integrated ECG, accelerometer and SpO2", Engineering in Medicine and Biology Society, http://ieeexplore.ieee.org/abstract/document/4649460/, Oct. 14, 2008.

Yilmaz, Tuba, et al.; "Detecting Vital Signs with Wearable Wireless Sensors", Department of Electronic Engineering, Queen Mary University of London, pp. 10837-10862, http://www.mdpi.com/1424-8220/10/12/10837/htm, Dec. 2, 2010.

Huang, Pengda; "Study on a Low Complexity ECG Compression Scheme with Multiple Sensors", Cornell University Library, https://arxiv.org/abs/1704.01612, Apr. 5, 2017.

* cited by examiner

SYSTEMS AND METHODS FOR SHIELDED AND ADJUSTABLE MEDICAL MONITORING DEVICES

CROSS-REFERENCE TO RELATED APPLICATIONS

This application claims priority to U.S. Patent Provisional Application No. 62/531,106, entitled "DISPOSABLE AND ADJUSTABLE VITAL SIGN MONITORING DEVICE", filed Jul. 11, 2017, which is herein incorporated by reference in its entirety.

BACKGROUND

The subject matter disclosed herein relates to shielded and adjustable medical monitoring device systems and methods. In particular, the subject matter disclosed herein relates to medical monitoring device systems that are shielded from certain operating conditions and are adjustable for patients of varying sizes.

Typically, clinical practice relies on protocols developed from medical knowledge. In various clinical settings, this medical knowledge is derived from the monitoring of physiological parameters and vital signs. In some instances, assessment of both the physiological parameters and vital signs plays an important role in not only the diagnosis of disease and/or physical conditions, but also in predictive diagnostics, for personalized medicine, and potentially in novel drug discovery. Further, in some instances, the medical monitoring devices may be worn by a patient. However, in some instances, the medical monitoring devices may operate in unfavorable conditions or be worn by patients of a variety of body shapes. Accordingly, it may be difficult to adjust the medical monitoring device to accommodate patients of various body sizes. Additionally, the medical monitoring devices may experience high attenuation interference from external devices in certain environments. Typically, reducing these attenuations requires heavy and bulky equipment that is expensive, and compromises the flexibility of the medical monitoring device to accommodate various body sizes.

BRIEF DESCRIPTION

In one embodiment, a system for monitoring medical conditions includes a conformable medical monitoring device. The conformable medical monitoring device includes a first substrate layer, which includes an electronics module, a plurality of signal traces, and at least one electrode, such that one or more of the plurality of signal traces electrically couple the at least one electrode to the electronics module. Furthermore, the conformable medical monitoring device includes a second substrate layer positioned over the electronics module, the first substrate layer, or any combination thereof, such that the second substrate layer insulates the electronics module, the first substrate layer, or any combination thereof. The conformable medical monitoring device also includes a third substrate layer positioned over the second substrate layer, such that the third substrate layer reduces electromagnetic interference caused by a voltage pulse. The conformable medical monitoring device also includes an adjustable system coupled to the first substrate layer, such that the adjustable system changes a position of the at least one electrode relative to the electronics module.

In another embodiment, a method for manufacturing a printed lead set with an electronics module for use in a medical monitoring device includes printing a plurality of conductive signal traces and a plurality of electrodes on a first conformable substrate layer, printing a second shielding substrate layer over the first conformable substrate layer, the plurality of conductive signal traces, the plurality of electrodes, or any combination thereof, and applying a third shielding substrate layer over the second shielding substrate layer, such that the third shielding substrate layer shields the first conformable substrate layer, the second shielding substrate layer, the plurality of conductive signal traces, the plurality of electrodes, or any combination thereof from electromagnetic interference.

In yet another embodiment, a conformable medical monitoring device includes a first substrate layer, which includes an electronics module, a plurality of signal traces, and at least one electrode, such that one or more of the plurality of signal traces electrically couple the at least one electrode to the electronics module. The medical monitoring device also includes a second substrate layer positioned over the electronics module, the first substrate layer, or any combination thereof. Furthermore, the medical monitoring device includes a resistor carrier that holds at least one resistor in place and fixes the second substrate layer to a third substrate layer.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
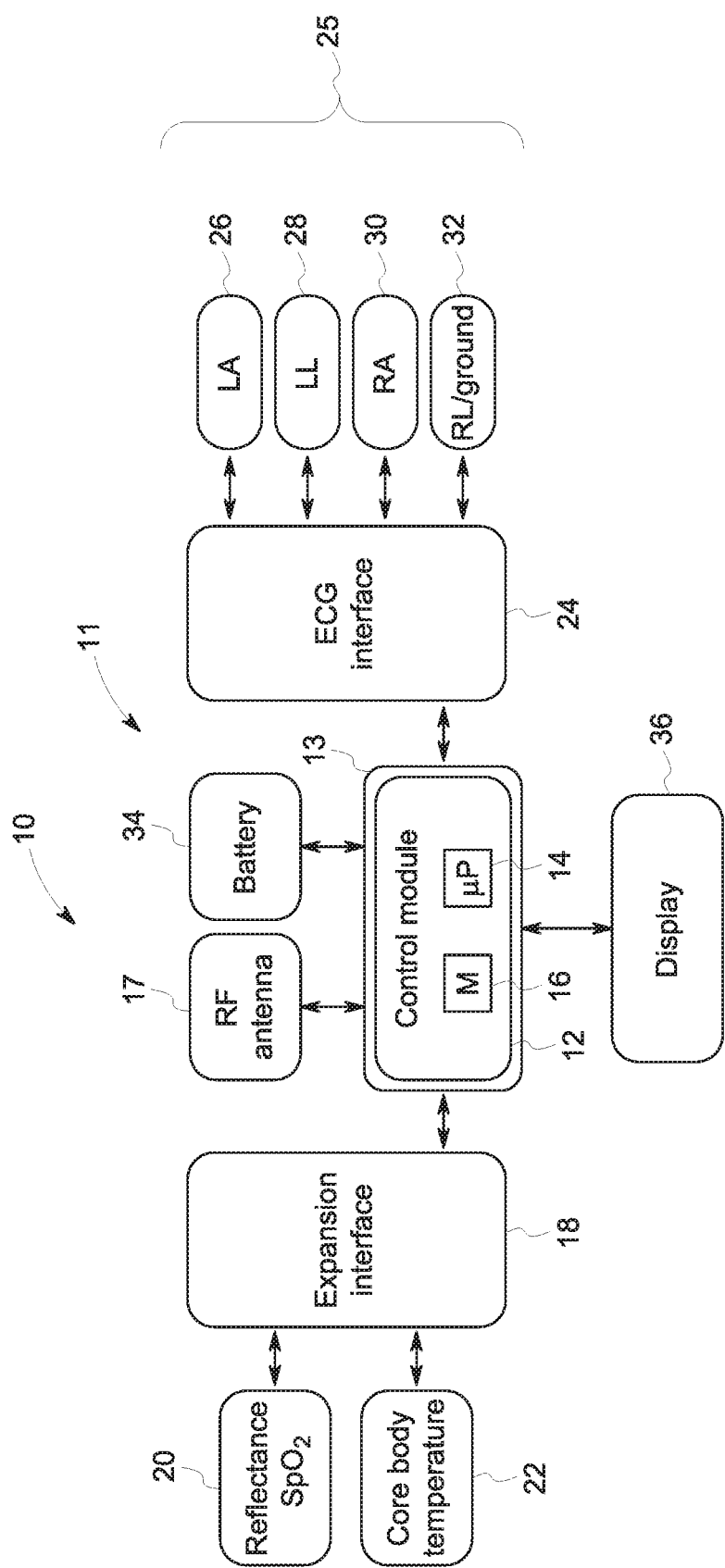
FIG. 1 is a block diagram of an embodiment of a medical monitoring device, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements.

Certain factors behind the demand for reliable low-cost wireless wearable medical monitoring devices include the lack or the shortage of centralized laboratories and medical facilities, the rise in the number of illness among older populations, the early diagnosis of diseases, personalized medicine, the use of companion tests for drug use, government initiatives, and insurance acceptance, among others. These factors may be a result of drawbacks of existing wired medical monitoring systems, which often limit patient mobility and patient access to caregivers while the devices are in place and coupled to patients in a wired manner, exacerbating the workload for healthcare providers. As a result, wireless patient monitoring systems may provide some improvements over conventional wired patient monitoring devices. However, current implementations of wireless patient monitoring systems may be too expensive and bulky, may lack the ability to personalize for various body types, may experience unwanted electromagnetic interference (EMI) in certain environments, may be uncomfortable to certain patients, and may require certain components to be replaced frequently, for example, in response to being exposed to a certain conditions (e.g., voltage pulses, EMI, etc.). Moreover, remedying these drawbacks of existing wireless medical monitoring systems may be difficult and time consuming.

While the following discussion is generally provided in the context of medical monitoring devices, such as vital motoring systems and bioparameter monitoring systems for use in certain medical application, the provision of examples and explanations in such a medical context is only to facilitate explanation by providing instances of real-world implementations and applications. Indeed, the low-cost, wearable monitoring devices discussed herein may render unique benefits not only for the medical field, but also for human performance and safety monitoring applications in athletics, military environment, security systems, and industrial settings, to name a few examples. The disclosed subject matter provides systems and methods associated with implementing shielding systems and/or adjustable systems useful in blood pressure sensors, pulse oximeter sensors, electromyography (EMG) sensors, inertial sensors, respiratory sensors, and other suitable biopotential and/or vital sensors.

Moreover, the present disclosure includes implementation of a low-cost, wireless, wearable medical monitoring device (hereinafter referred to as a "medical monitoring device") in various hospital settings. For example, the embodiments of the present disclosure may be implemented to provide a continuum of care in an intensive care unit (ICU) environment, in a general ward (GW) environment, in a home care, among others. The embodiments of the present disclosure may be implemented to be used by the hospitalized population, as the medical monitoring devices may be worn by and remain attached to the patient during various stages of treatment. In some embodiments, the medical monitoring device may be implemented during recovery and may generate alarms for various interventions as well as link with the electronic medical records. Additionally, the medical monitoring devices may reduce patient exposure to certain disease causing agents, and the need for constant sterilization, as the medical monitoring device disclosed herein may be used by one patient and then disposed of. Furthermore, the medical monitoring device may eliminate wires, which not only may untether the patients from the equipment, allowing them greater mobility and comfort, but may also make the workflow for care providers and monitoring device management more efficient. In some instances, the medical monitoring device facilitates earlier patient discharge from hospitals, for example, due to early and safe patient mobilization facilitated by wireless medical monitoring devices.

In some embodiments, the ability to reposition the electrodes is important, for example, to reduce skin irritation, improve signal trace quality, and reduce alarm rates. Typically, repositionable electrodes rely on solid conductive gel adhesives positioned on various breathable substrates. The degree of electrode lifetime and number of repositions varies across manufactures, often requiring various procedural steps (e.g., re-wetting the adhesive) to enhance longevity. In some instances, the durability of the adhesion of the electrode to the skin is a combination of the properties of the adhesive material and of the substrate, often requiring consideration of morphologies and moisture transport rates. To achieve a repositionable lead-set (e.g., a substrate assembly), the integration of these material properties is considered in the medical monitoring device design and manufacturing plan. As discussed herein, repositionable conductive hydrogel electrode materials are deposited on the medical monitoring device. Additionally, a non-conductive adhesive may be incorporated around the conductive adhesive electrode to improve adhesion subsequent to repositioning.

The concept of a disposable, conformable, and high performing medical monitoring device with multi-parameter sensing capabilities that can be adjusted to different body shapes and sizes is disclosed. The disposable and adjustable vital sign monitoring device may include a multi-sensor electronics module (hereinafter referenced as the "electronics module") and a flexible adjustable lead-set. In some embodiments, the electronics module may include a shielding component that protects certain aspects of the electronics module, as discussed in detail below. Furthermore, the flexible adjustable lead set may provide patient comfort and care-giver workflow benefits. In some embodiments, the medical monitoring device may be disposable, such that the medical monitoring device may be used by one patient and disposed of after use. Further, the medical monitoring device may provide ubiquitous patient monitoring solutions in various clinical settings. While the embodiments disclosed herein include an electronics module with specific components, it should be noted that the embodiments disclosed herein may be used in conjunction with electronics modules including any additional or alternative components, such as light emitting diode (LED) lights, thermistors, and transceivers, just to name a few.

By way of introduction, FIG. 1 is a schematic diagram of an embodiment of a medical monitoring device 10, in accordance with aspects of the present disclosure. In the illustrated embodiment, various components of the electronics module 11 of the medical monitoring device 10 are depicted. In the illustrated embodiment, the medical monitoring device 10 includes a control module 12. The control module 12 may be fabricated on a miniaturized rigid printed circuit board (PCB) (e.g., FR4) or a flexible (e.g., polyimide or polyethylene terephthalate) based substrate. The control module 12 may then be attached to (or integrated with) a flexible lead set 13 (e.g., signal traces, wires), as discussed in detail below. Further, in the illustrated embodiment, the control module 12 includes a processor 14 that may execute instructions stored in a memory device 16 to perform operations, such as determine various physiological parameters. In some instances, the processor 14 may include one or more general purpose microprocessors, one or more application specific processors (ASICs), one or more field programmable logic arrays (FPGAs), or any combination thereof. Additionally, the memory device 16 may be a tangible, non-transitory, computer-readable medium that store instructions executable by and data to be processed by the processor 14. For example, in the depicted embodiment, the memory device 16 may store algorithms that are executed by the processor 14. Thus, in some embodiments, the memory device 16 may include random-access memory (RAM), read-only memory (ROM), rewritable non-volatile memory, flash memory, hard drives, optical discs, and the like.

It should be noted that, in some embodiments, the control module 12 may be external to the medical monitoring device 10, such that the medical monitoring device 10 is in electrical communication with the external control module. As such, patient data may be transmitted via a wired or wireless link to an external processor that includes the computing power and bandwidth to analyze the patient data arriving from the link. Furthermore, in some embodiments, processor 14 and memory device 16 may be used by the medical monitoring device 10, in addition to using external processors and memory devices, for example, to facilitate determining patient data, such as physiological parameters. In other instances, the patient data is transmitted wirelessly to a hospital's communication infrastructure (e.g., Wi-Fi network, local area network (LAN), wide area network (WAN), etc.), using a long range radio (such as Wi-Fi radio). A radio frequency (RF) antenna 17 may facilitate the wireless communication with the hospital's communication infrastructure.

In the illustrated embodiment, the medical monitoring device 10 includes an expansion interface 18 that may enable the control module 12 to interface with various sensors. For example, the expansion interface 18 may enable the control module 12 to interface with a reflective pulse oximetry sensor 20 (e.g., the illustrated SpO$_2$ sensor 20) that may provide a reading of peripheral oxygen saturation levels. Additionally or alternatively, in the illustrated embodiment, the expansion interface 18 may enable the control module 12 to interface with a core body temperature sensor 22. It should be noted that in some embodiments, the expansion interface 18 may include many ports to enable the control module 12 to interface with any other suitable device (e.g., sensors for vital signs such as impedance-based respiration or non-invasive blood pressure measurement). In some embodiments, the ports may be omitted from the expansion interface 18, such that the expansion interface 18 enables wireless connectivity.

In the illustrated embodiment, the medical monitoring device 10 includes an electrocardiography (ECG) interface 24. The ECG interface 24 may involve recording electrical activity associated with the heart of a patient over a period of time using any number of electrodes 25 in contact with the skin. For instance, a conventional twelve-lead ECG device may include ten electrodes placed on the limbs of a patient and on the surface of the chest. The overall magnitude of the electrical potential of the heart may be measured from multiple different angles and recorded over a period of time to capture the overall magnitude and the direction of the heart's electrical depolarization at each moment through the cardiac cycle. In the illustrated embodiment, the ECG interface 24 includes four electrodes 25 that support six leads. In particular, in the illustrated embodiment, the ECG interface 24 supports a left arm (LA) electrode 26, a left leg (LL) electrode 28, a right arm (RA) 30, and a right leg (RL) electrode 32. However, it should be understood that the ECG interface 24 may include any number of electrodes that support and number of leads. The RL electrode may be the ground. However, in some embodiments, the RL electrode may be a reference potential other than the ground. As described in detail below, two electrodes may be positioned on each side placed at clavicle height, one electrode may be placed low on the rib-cage, and another electrode (e.g., the RA electrode 30) below the pectoral muscle to the fourth intercostal space. In addition to supporting multiple leads, it should be noted that in some embodiments, the ECG interface 24 may support a single lead.

In the illustrated embodiment, the medical monitoring device 10 includes a battery 34. In some embodiment, the battery 34 is a disposable battery, such as an Air Zinc battery. It should be noted that in some embodiments, the battery 34 may be any suitable device used to power the control module 12, such as a printed battery and the like. The battery 34 may supply electrical power to the electronics module 11 and its various components. In other embodiments, the power source may be provided via a wired link, e.g., the link to an external control module 12. The medical device 10 may include a display 36. In other embodiments, the display 36 may be part of an external device and may be external to the medical monitoring device 10. The display 36 may present information, such as the bioparameters and vital parameters to a user. The display 36 may be a liquid crystal display (LCD), an electroluminescent display (ELD), a cathode ray tube display (CRT), and/or a LED display, etc. Furthermore, in some embodiments, the display 36 may be a touch screen device that includes various haptic sensors that receive tactile inputs.

Traditional ECG or respiration electrode arrays include a disposable skin-contacting electrode connected to a shielded, insulated wire, in turn connected to the rack-mounted electronics module 11. The size of the lead set is generally not a major concern, because in some instances the electronics module may be large. As ECG and other electrode-based applications, such as impedance respiration rate technology, transition to wireless systems or body-worn monitoring systems, sizing the signal traces or lead set 13 to an individual's body may reduce tension, prevent snagging, and eliminate entangling of the lead set on the patient, their clothes, and/or other medical equipment. Printed lead sets enable a host of new device shapes (in addition to facilitating manufacturing efficiencies). For example, the lead sets may be printed using silk printing, rotary press printing (e.g., offset printing, ink jet printing, laser printing, etc.), or any other suitable printing process. There are many options for varying the length of a printed lead set including adhesives, serpentine shapes, coiling and folding, as discussed in detail below.

Figure 2:
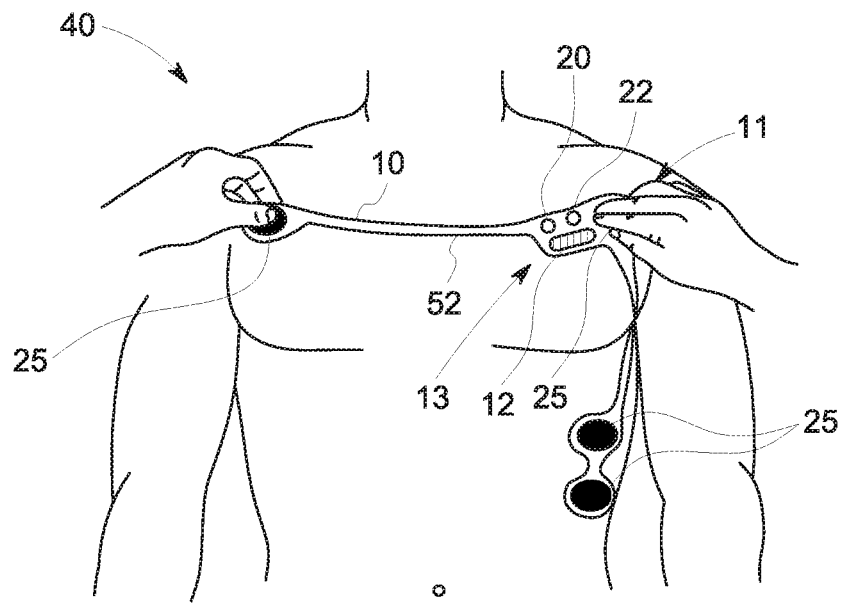
FIG. 2 is a schematic diagram of an embodiment of a first placement configuration of the medical monitoring device of FIG. 1, in accordance with aspects of the present disclosure.
Figure 3:
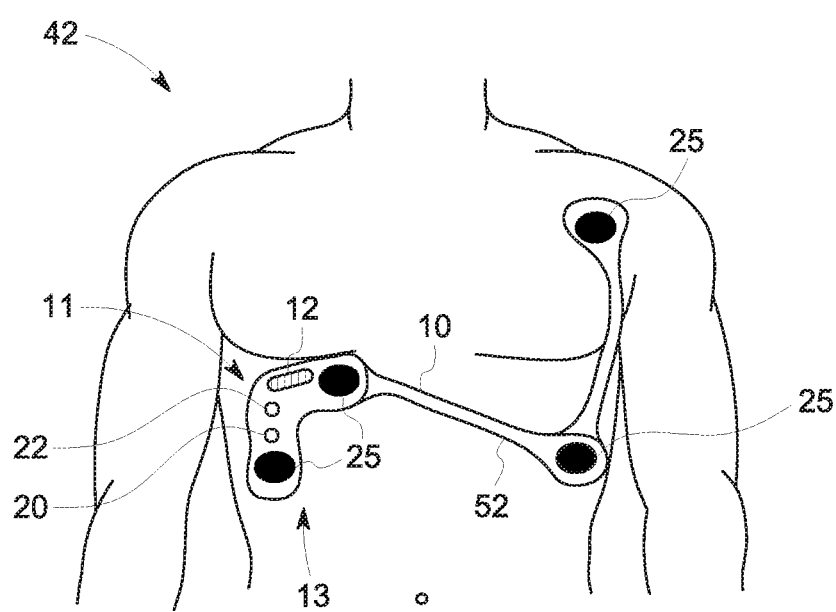
FIG. 3 is a schematic diagram of an embodiment of a second placement configuration of the medical monitoring device of FIG. 1, in accordance with aspects of the present disclosure.
Figure 4:
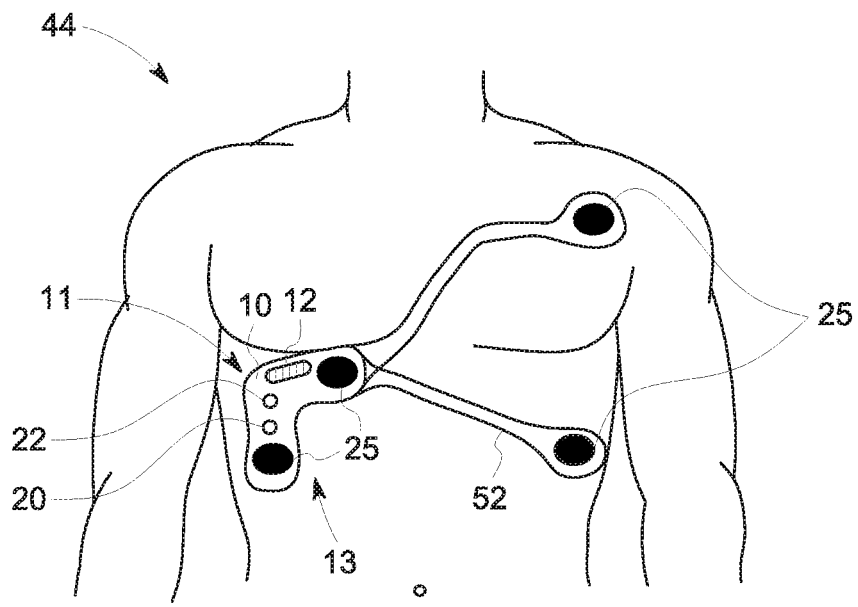
FIG. 4 is a schematic diagram of an embodiment of a third placement configuration of the medical monitoring device of FIG. 1, in accordance with aspects of the present disclosure.
Figure 5:
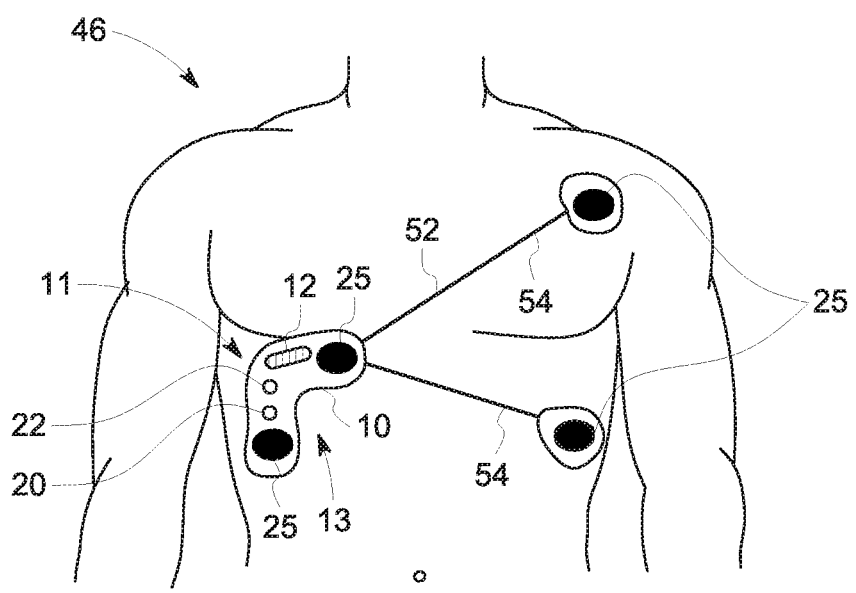
FIG. 5 is a schematic diagram of an embodiment of a fourth placement configuration of the medical monitoring device of FIG. 1, in accordance with aspects of the present disclosure.
Figure 6:
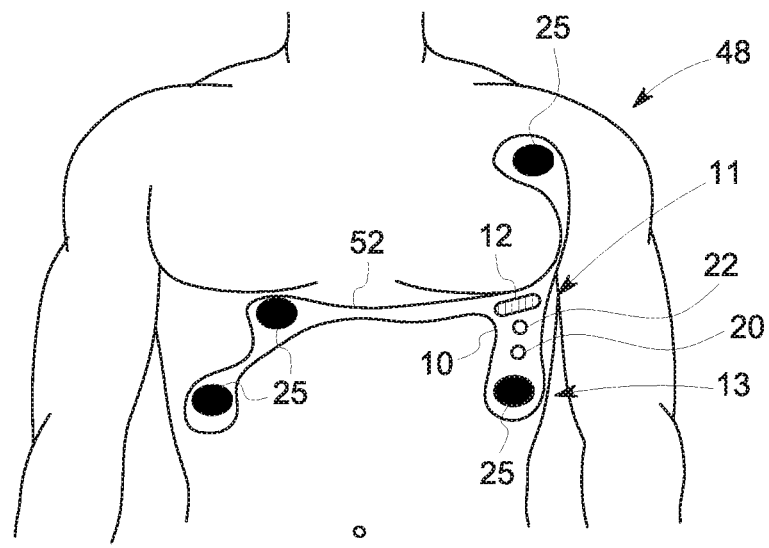
FIG. 6 is a schematic diagram of an embodiment of a fifth placement configuration of the medical monitoring device of FIG. 1, in accordance with aspects of the present disclosure.
Figure 7:
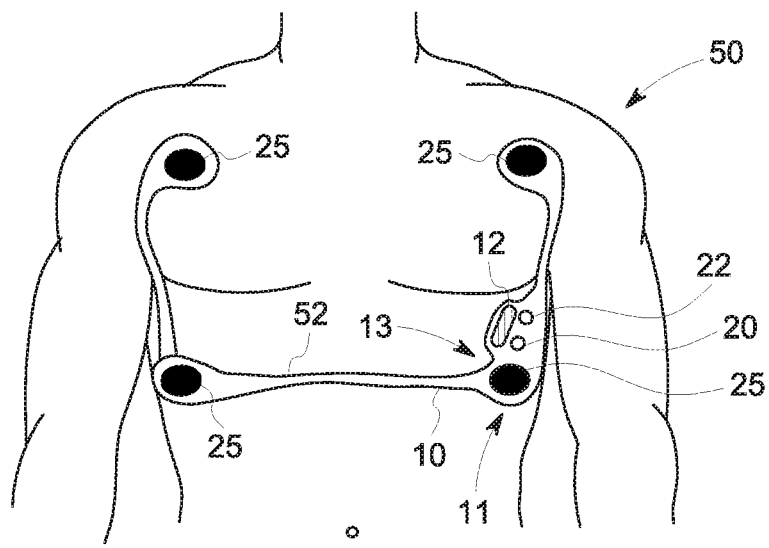
FIG. 7 is a schematic diagram of an embodiment of a sixth placement configuration of the medical monitoring device of FIG. 1, in accordance with aspects of the present disclosure.

FIGS. 2-7 each depict a schematic diagram of an embodiment of a configuration of the medical monitoring device 10 of FIG. 1, in accordance with aspects of the present disclosure. Specifically, FIG. 2 depicts a schematic diagram of an embodiment of a first placement configuration 40 of the medical monitoring device 10, FIG. 3 depicts a schematic diagram of an embodiment of a second placement configuration 42 of the medical monitoring device 10, FIG. 4 depicts a schematic diagram of an embodiment of a third placement configuration 44 of the medical monitoring device 10, FIG. 5 depicts a schematic diagram of an embodiment of a fourth placement configuration 46 of the medical monitoring device 10, FIG. 6 depicts a schematic diagram of an embodiment of a fifth placement configuration 48 of the medical monitoring device 10, and FIG. 7 depicts a schematic diagram of an embodiment of a sixth placement configuration 50 of the medical monitoring device 10. While in the illustrated embodiments the placement of the electrodes 25 (e.g., the LA electrode 26, the LL electrode 28, the RA electrode 30, the RL electrode 32) on the sternum is shown, in some embodiments, other design concepts for different anatomical region placements are used. In the illustrated embodiments, the medical monitoring device 10 may include an adjustable system 52 to enable the medical monitoring device 10 to adjust to a variety of body shapes and sizes. The adjustable system 52 may facilitate the adjustment of the placement of the electrodes 25 on the patient, as described in detail below.

In the illustrated embodiment, the medical monitoring device 10 includes the electronics module 11 that includes three leads which support four electrodes 25 (e.g., LA, LL, RA, and RL electrodes), in which two electrodes 25 are placed at clavicle height, one electrode is placed low on the rib-cage, and another electrode (e.g., the RA electrode) is positioned below the pectoral muscle to the forth intercostal space. The position of the reference electrode may be combined with at least one other electrode without need for a variable length connector. Further, in the illustrated embodiment, the $SpO_2$ sensor 20 and the core body temperature 22 (e.g., the coulomb blockade thermometer (CBT) sensor), along with at least one electrode may be incorporated, into a single patch to reduce the number of variable-length connections.

In some instances, the first placement configuration 40 and the sixth placement configuration 50 may be the arrangement of the medical monitoring device 10, since the first and sixth placement configuration 40, 50 show embodiments with 3-lead ECG and traditional lead placement, while the others show Modified Chest Lead (MCL1) placement. In the illustrated embodiment, the fourth placement configuration 46 utilizes a wire 54 (e.g., a signal trace) to connect the remote electrodes 25 in place of a printed lead set 13. In some instances, the first placement configuration 40 is the preferred placement configuration because it places the $SpO_2$ sensor 20 and the core body temperature sensor 22 at the clavicle where the lack of sub-cutaneous tissue may lead to a better signal.

Figure 8:
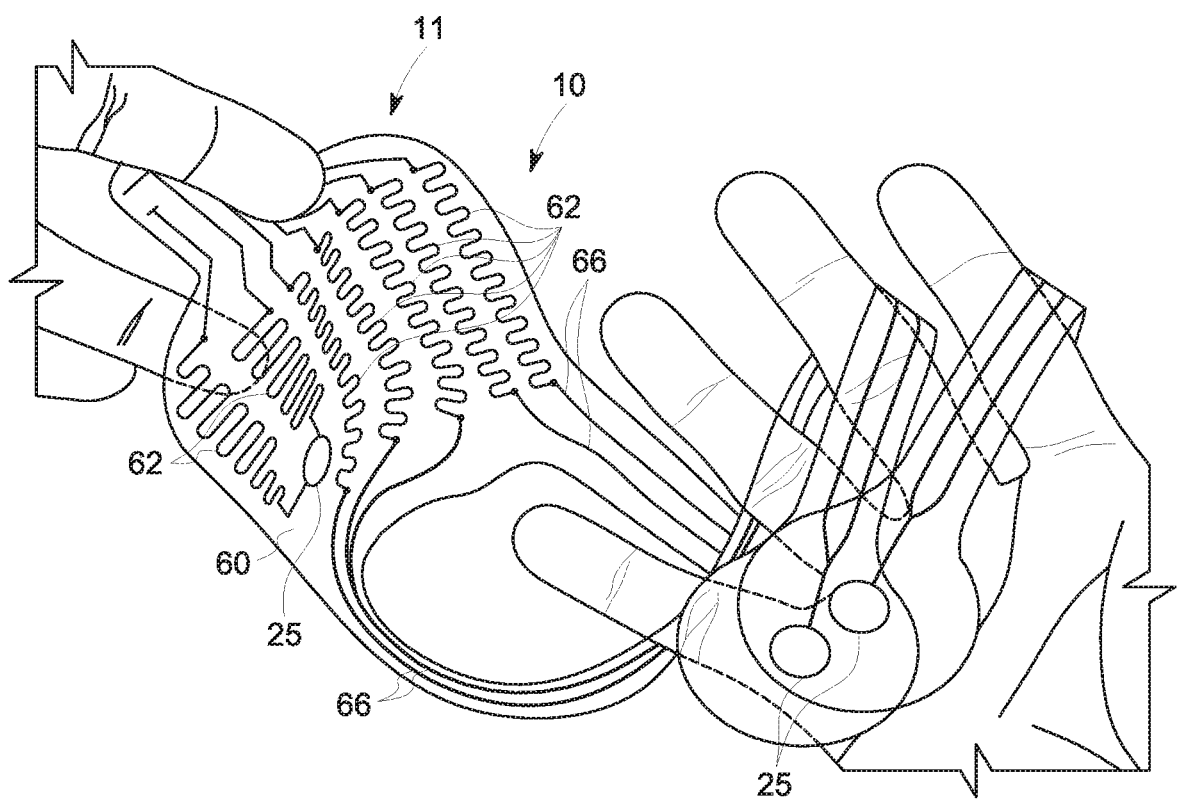
FIG. 8 is a schematic diagram of an embodiment of the medical monitoring device of FIG. 1, such that at least a portion of the medical monitoring device is printed on a substrate, in accordance with aspects of the present disclosure.

FIG. 8 is a schematic diagram of an embodiment of the medical monitoring device 10 of FIG. 1, wherein at least a portion of the medical monitoring device 10 is printed on a substrate 60, in accordance with aspects of the present disclosure. In the illustrated embodiment, the medical monitoring device 10 includes a variety of resistors 62, electrodes 25, and signal traces 66 (e.g., wiring) printed on the substrate 60. In some embodiments, the substrate 60 may be the lead set 13. In some embodiments, the resistors 62 may be coated with any suitable ink that may be printed onto the substrate 60, e.g., a polymer substrate. Further, the electrodes 25 and signal traces 66 may be printed with a conductive ink, e.g., silver chloride (AgCl) ink electrodes 25, while the signal traces 66 may be printed with silver (Ag) ink. The substrate 60 may be polyimide-based, polyethylene terephthalate-based (PET-based), thermoplastic polyurethane-based (TPU-based), and the like. As illustrated, the medical monitoring device 10 may be foldable and stretchable.

Figure 9:
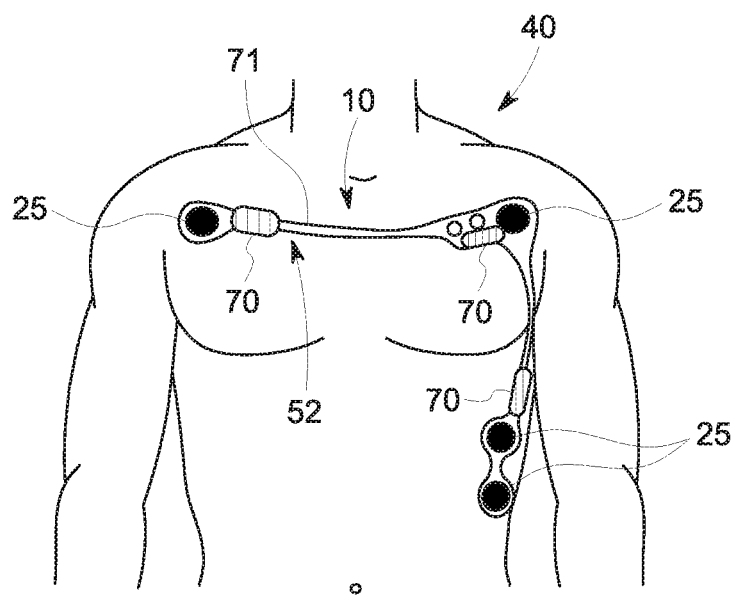
FIG. 9 is a schematic diagram of another embodiment of the first placement configuration of FIG. 2, including an adjustable system in accordance with aspects of the present disclosure.
Figure 10:
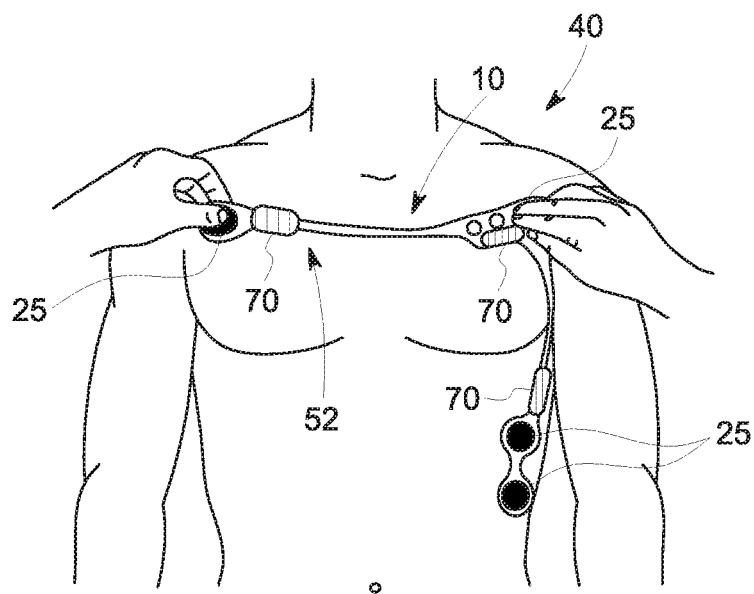
FIG. 10 is a schematic diagram of another embodiment of the first placement configuration of FIG. 2, depicting modifying the adjustable system of FIG. 9, in accordance with aspects of the present disclosure.
Figure 11:
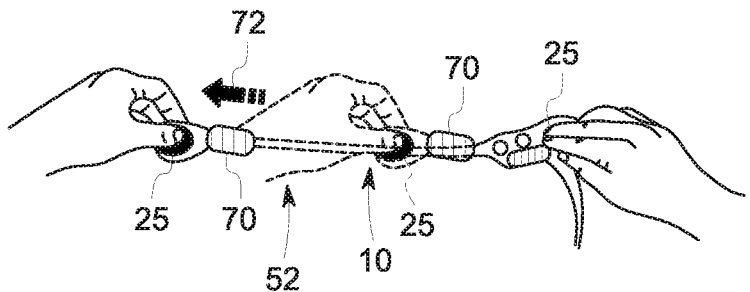
FIG. 11 is a schematic diagram of another embodiment of the first placement configuration of FIG. 2, whereby the adjustable system of FIG. 9 is adjusted, in accordance with aspects of the present disclosure.
Figure 12:
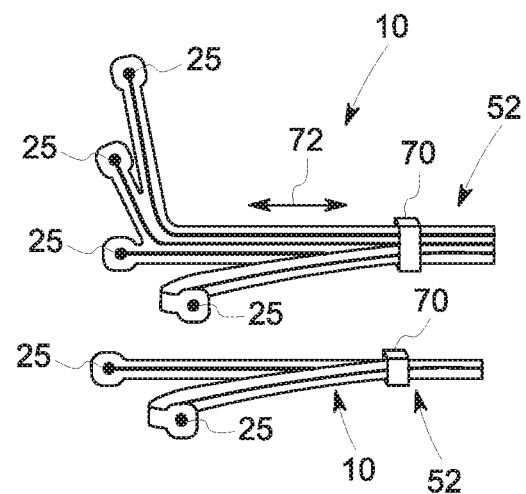
FIG. 12 is a schematic diagram of another embodiment of the adjustable system of FIG. 9 employed in the placement configurations of FIGS. 2-7, in accordance with aspects of the present disclosure.
Figure 13:
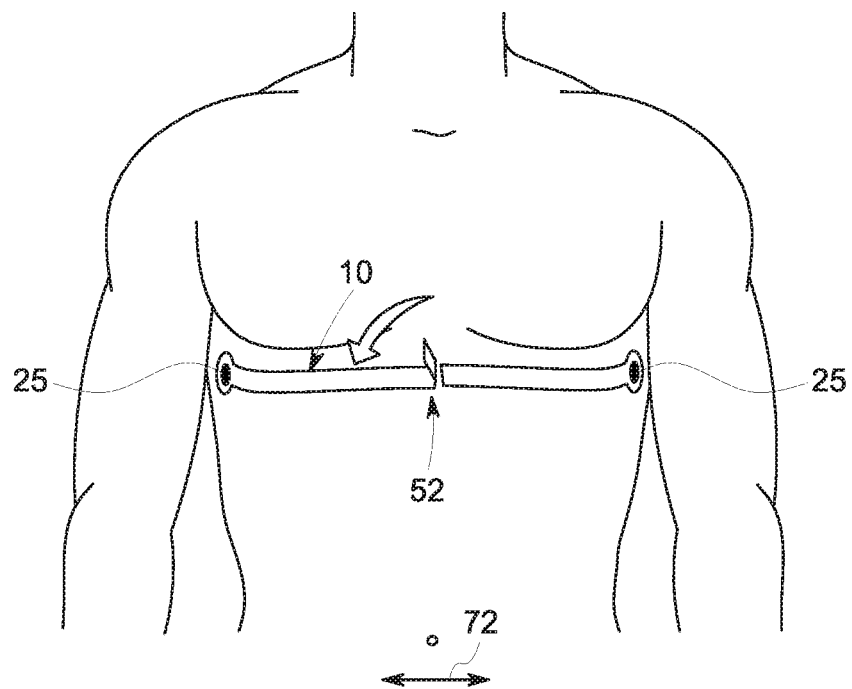
FIG. 13 is a schematic diagram of another embodiment of the adjustable system of FIG. 9 employed in the placement configurations of FIGS. 2-7, in accordance with aspects of the present disclosure.

FIGS. 9-16 each depict a schematic diagram of another embodiment of the placement configurations 40, 42, 44, 46, 48, 50 of FIG. 2 and/or the adjustable system 52 of FIG. 9, including an adjustable member 70 in accordance with aspects of the present disclosure. A key material challenge created by many of the geometries of the placement configurations 40, 42, 44, 46, 48, 50 is the potential for folding to occur with small radii of curvature (e.g., 180° fold-back) which may limit the lifetime of the printed components of the lead set 13 or electronics module 11. The schematic diagrams illustrate how the medical monitoring device 10 may adjusted (e.g., folded) to be placed on a patient and how the medical monitoring device 10 may be adjusted on a patient via the adjustable system 52. For example, the medical monitoring device 10 may include any suitable number of adjustable members 70 that may enable the medical monitoring device 10 to be adjusted along a direction 72. In the illustrated embodiments of FIGS. 9-12, the direction 72 is along the distance between two electrodes 25, such that the adjustable member 70 enables the medical monitoring device 10 to adjust and accommodate various body types and sizes. In FIGS. 12 and 13, the medical monitoring device includes the adjustable system 52 that includes the adjustable member 70. The adjustable member 70 may enable the adjustment of each of the electrodes 25 by individually enabling the electrodes 25 to be adjusted along the direction 72. In some embodiments, the medical monitoring device 10 may wrap around the patient, and may be adjusted to accommodate patients of various body sizes and shapes. For example, the adjustable member 70 may be configured to adjust a length of one or more straps 71 of the medical monitoring device 10, e.g., along the direction 72.

Figure 14:
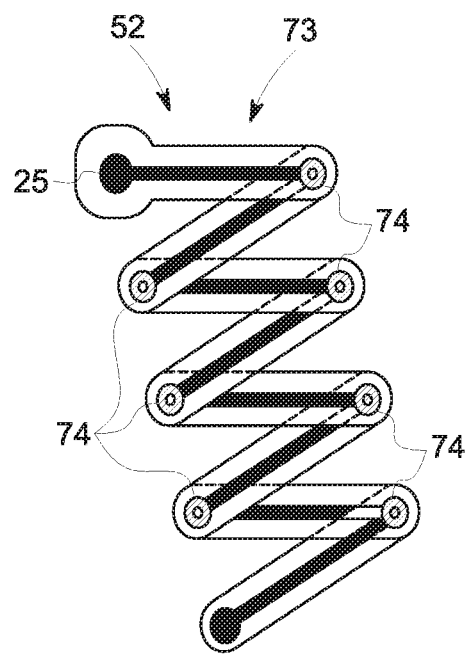
FIG. 14 is a schematic diagram of another embodiment of the adjustable system of FIG. 9, including a variety of linkage nodes, in accordance with aspects of the present disclosure.
Figure 15:
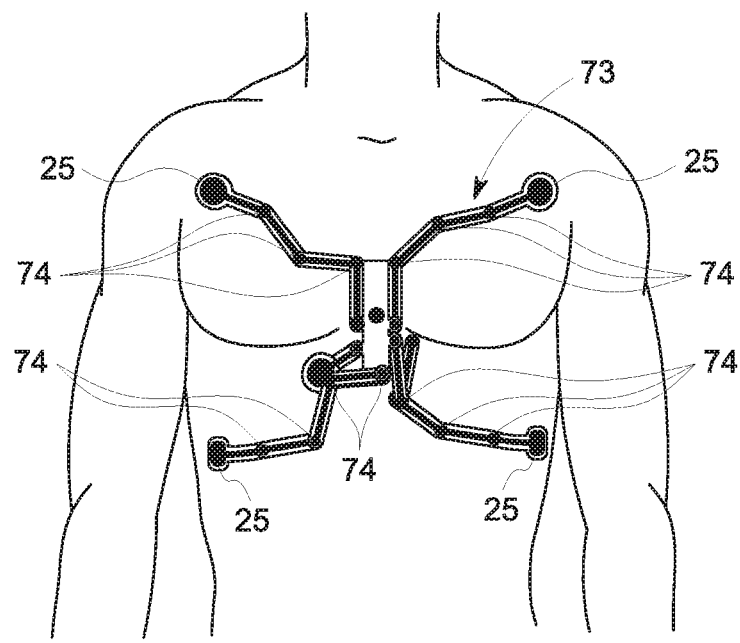
FIG. 15 is a schematic diagram of another embodiment of the adjustable system of FIG. 9 as worn by a patient, including the variety of linkage nodes of FIG. 14, in accordance with aspects of the present disclosure.
Figure 16:
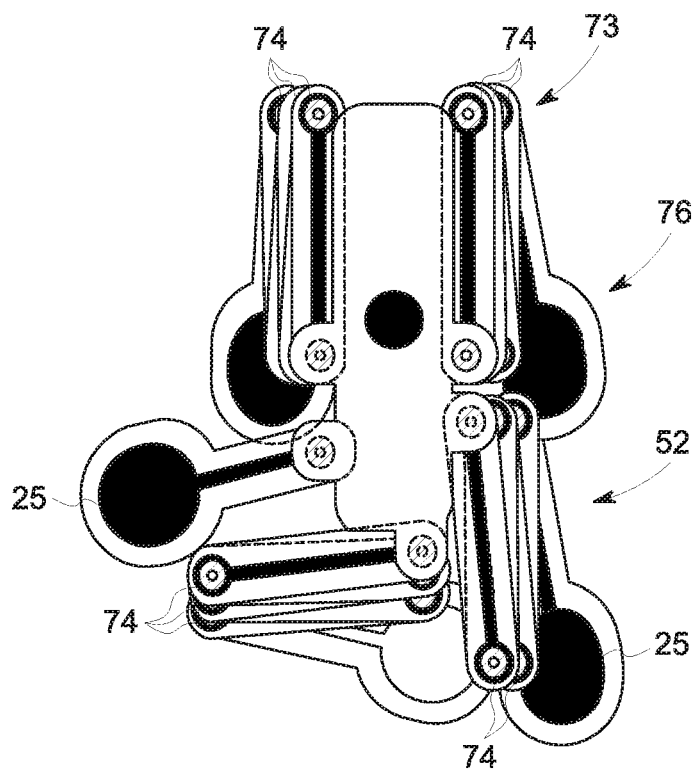
FIG. 16 is a schematic diagram of another embodiment of the adjustable system of FIG. 9 in a compact, folded state, including the variety of linkage nodes of FIG. 14, in accordance with aspects of the present disclosure.
Figure 17:
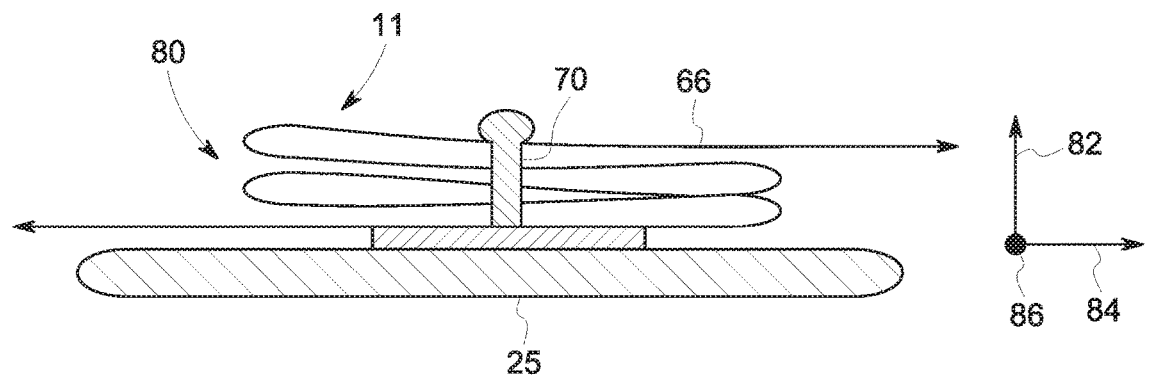
FIG. 17 is a side view of another embodiment of the adjustable system 52 of FIG. 9, employing a serpentine arrangement, in accordance with aspects of the present disclosure.
Figure 18:
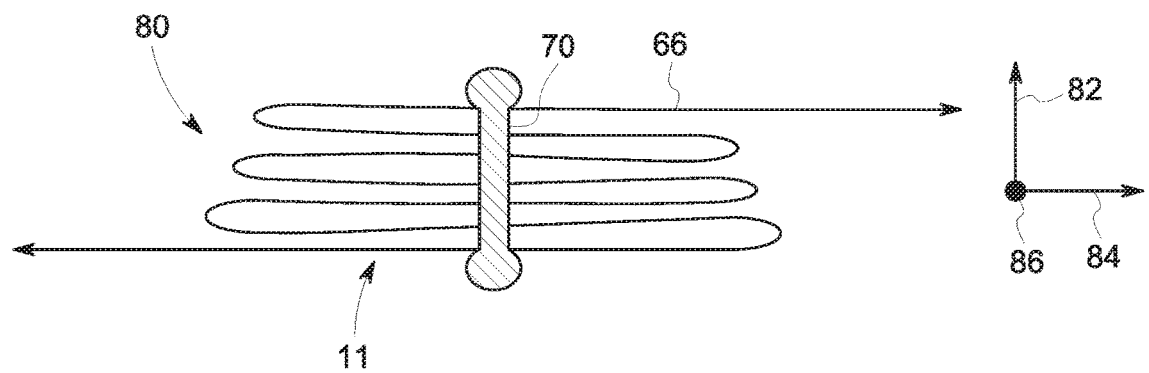
FIG. 18 is a side view of another embodiment of the adjustable system of FIG. 9, employing the serpentine arrangement of FIG. 17, in accordance with aspects of the present disclosure.
Figure 19:
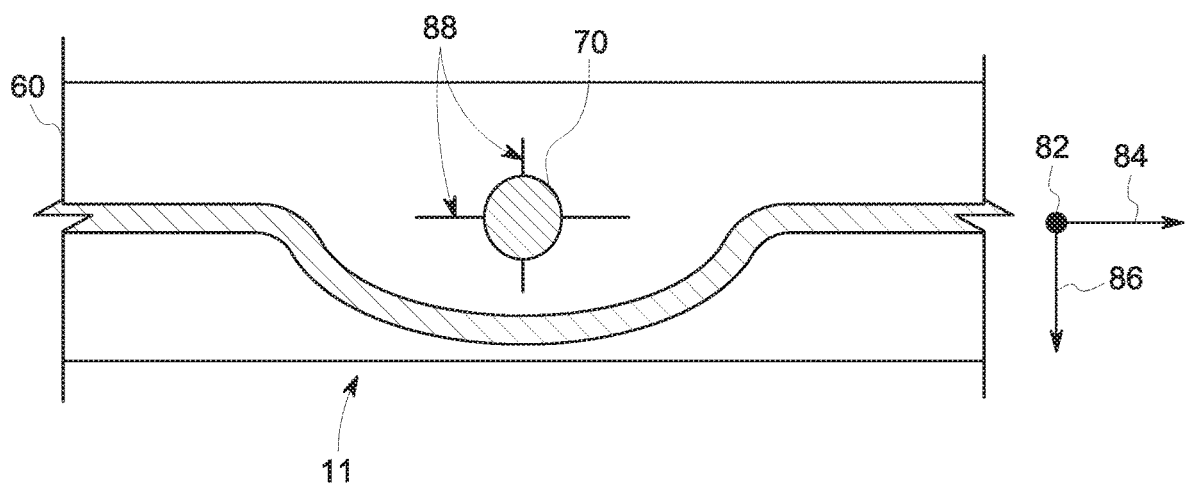
FIG. 19 is a top view of another embodiment of the adjustable system of FIG. 9, employing the serpentine arrangement of FIG. 17, in accordance with aspects of the present disclosure.
Figure 20:
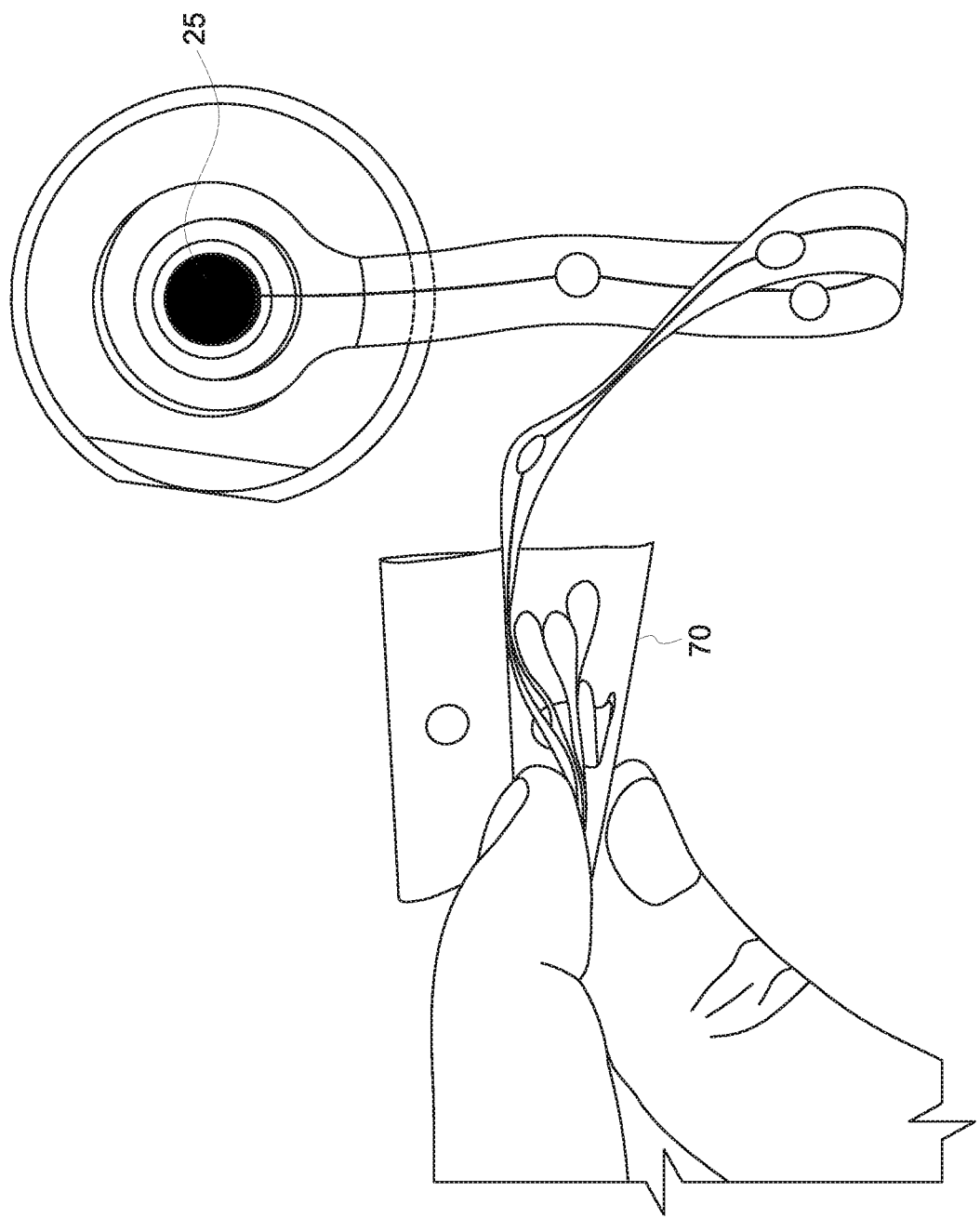
FIG. 20 is a schematic diagram of another embodiment of the adjustable system of FIG. 9, employing the serpentine arrangement of FIG. 17, in accordance with aspects of the present disclosure.
Figure 21:
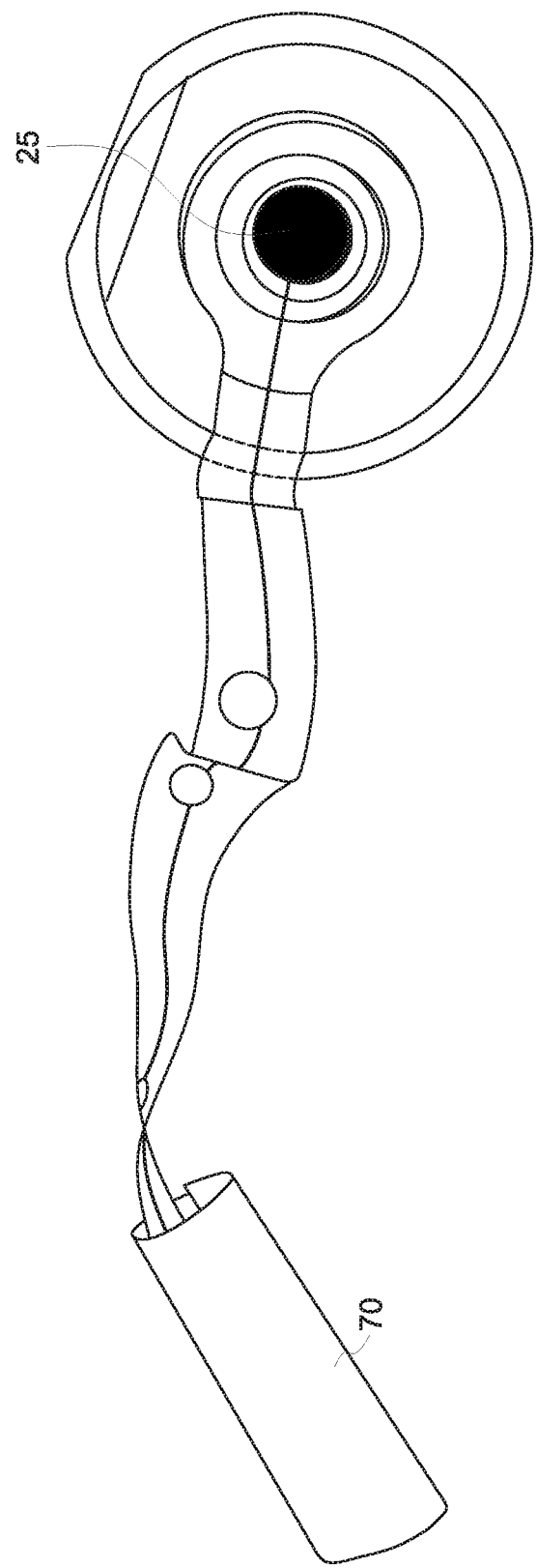
FIG. 21 is a schematic diagram of another embodiment of the adjustable system of FIG. 9, such that the serpentine arrangement of FIG. 17 is extended, in accordance with aspects of the present disclosure.

The placement configurations 40, 42, 44, 46, 48, and 50 may be achieved employing the chain length structure 73 illustrated in FIGS. 14-16. The chain length structure 73 may function as the adjustable system 52. A variety of linkage-nodes 74 may be used to enable the electrodes 25 to extend and retract. Furthermore, the chain length structure 73 illustrated in FIGS. 14-16 may enable the medical monitoring device 10 to fold into a compact structure 76.

FIGS. 17-21 each depict a schematic diagram of another embodiment of the adjustable system 52 of FIG. 9, employing a serpentine arrangement 80, in accordance with aspects of the present disclosure. In the illustrated embodiments, the adjustable system 52 may include an adjustable member 70 that secures the lead set 13 (e.g., the folded signal trace 66, the folded substrate 60, etc.). In some embodiments, the adjustable member 70 is a pin (e.g., an elastomer pin) that may secure the folded signal trace 66 or the folded substrate along a vertical axis 82, such that the vertical axis 82 is orthogonal to the skin of a patient. In some instances, the skin of the patient may form a plane spanned by a lateral axis 84 and a longitudinal axis 86, which are each perpendicular with respect to each other. In the illustrated embodiment, the signal traces 66 may be pulled along the lateral axis 84 to lengthen and unfold the signal traces 66. In some embodiments, the adjustable member 70 may be secured to the electrode 25 at a first vertical end and secured to the folded signal traces 66 at a second vertical end. In other embodiments, the adjustable member 70 may be secured to the folded signal traces 66 at the first and second vertical ends. Furthermore, the adjustable member 70 may be secured to openings 88 (e.g., slits) on the substrate 60.

Figure 22:
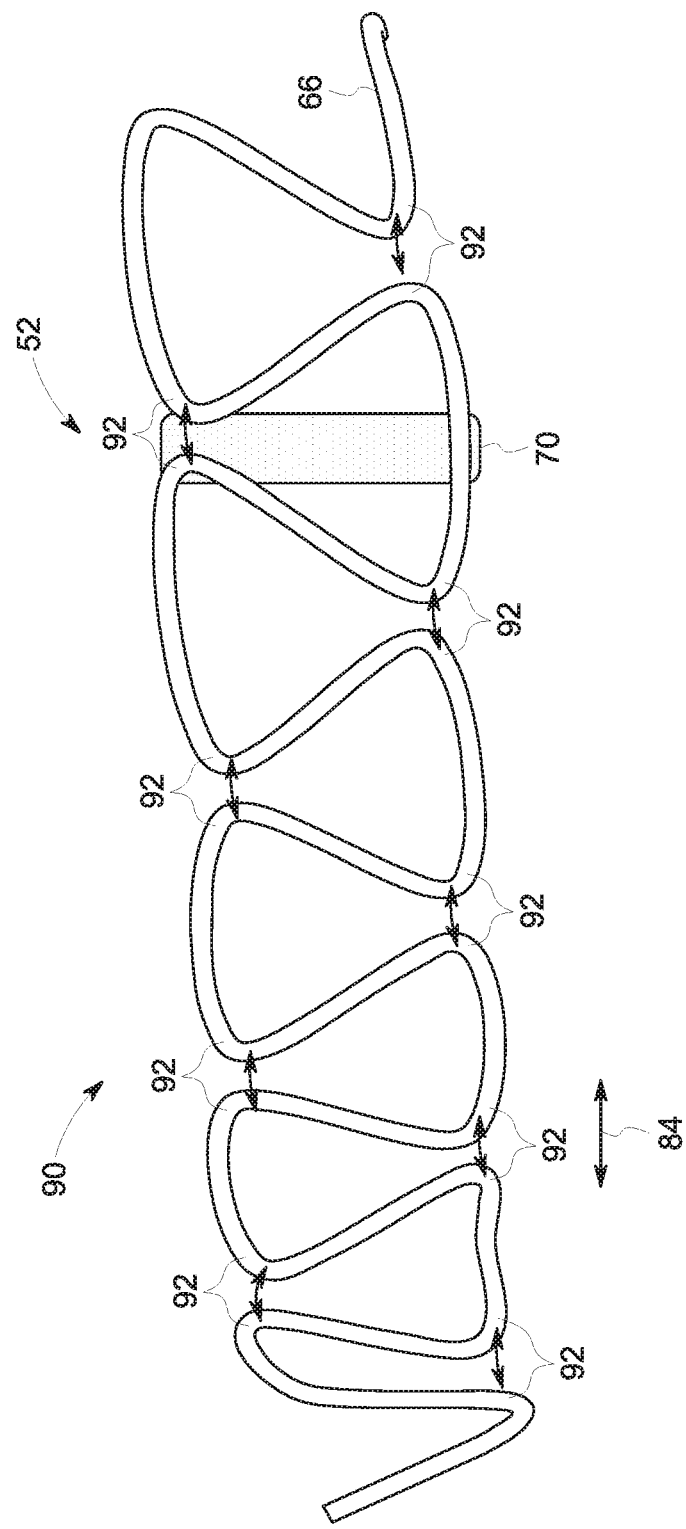
FIG. 22 is a schematic diagram of another embodiment of the adjustable system of FIG. 9, employing another serpentine arrangement, in accordance with aspects of the present disclosure.

FIG. 22 is a schematic diagram of another embodiment of the adjustable system 52 of FIG. 9, employing another serpentine arrangement 90, in accordance with aspects of the present disclosure. In the illustrated embodiment, the signal traces 66 are folded, such that folds 92 are formed and joined to form weak connections that may be broken, for example, when the signal traces 66 are extended. In the illustrated embodiment, the signal traces 66 are extended along the lateral axis 84. In addition, the adjustable system 52 may include any suitable adjustable members 70 that may secure a variety of folds 92 together after the weak connections between the folds are broken. In some embodiments, the connections formed by the adjustable member 70 may be stronger than those formed by the weak connections joining the folds 92. It should be noted that in some embodiments, the adjustable member 70 may be omitted.

Figure 23:
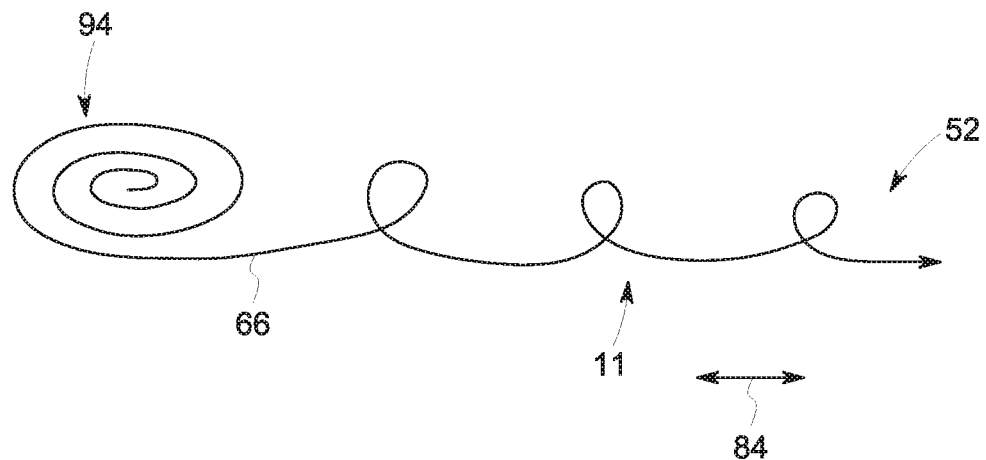
FIG. 23 is a schematic diagram of another embodiment of the adjustable system of FIG. 9, employing a spiral arrangement, in accordance with aspects of the present disclosure.

FIG. 23 is a schematic diagram of another embodiment of the adjustable system 52 of FIG. 9, employing a spiral arrangement 94, in accordance with aspects of the present disclosure. In the illustrated embodiment, the signal traces 66 are arranged in the spiral arrangement 94. The spiral arrangement 94 may unwind when the signal trace 66 is extended along the lateral axis 84. In some embodiments the lead set 13 may fold into the spiral arrangement 94.

Figure 24:
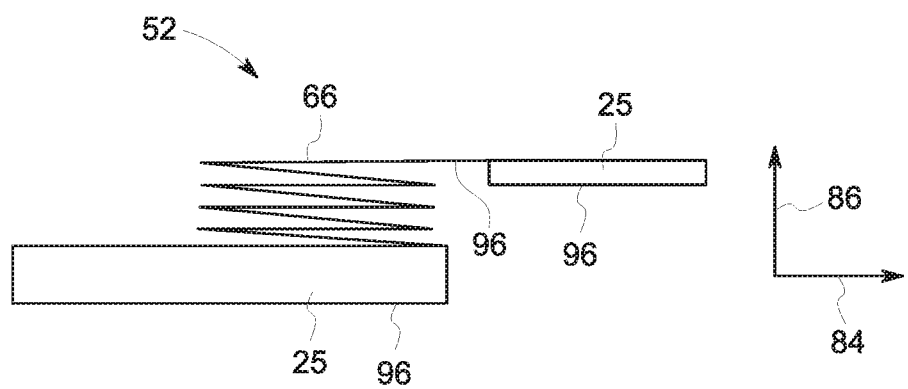
FIG. 24 is a schematic diagram of another embodiment of the adjustable system of FIG. 9, employing an adhesive member, in accordance with aspects of the present disclosure.
Figure 25:
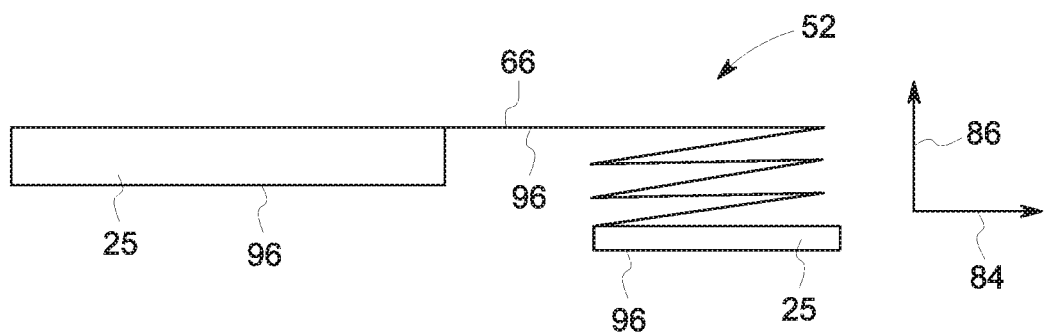
FIG. 25 is a schematic diagram of another embodiment of the adjustable system of FIG. 9, employing the adhesive member of claim 24, in accordance with aspects of the present disclosure.

FIGS. 24 and 25 each include a schematic diagram of another embodiment of the adjustable system 52 of FIG. 9, employing an adhesive member 96, in accordance with aspects of the present disclosure. In some embodiments, the adhesive member 96 may facilitate attachment of the medical monitoring device 10 to the patient. For example, the adhesive member 96 may be composed of certain polymer gels (e.g., silicone, polybutadiene, etc.), Velcro™, certain hydrogels, certain hydrocolloids, or any other adhesive material. In the illustrated embodiment, the adhesive member 96 is positioned on the surface of the electrodes 25 in contact with the patient and on the surface of the signal traces 66 in contact with the patient. In the illustrated embodiment, the adhesive member 96 is positioned on the electrodes 25 and the signal traces 66 along the vertical axis 86 facing toward the skin of a patient. However, it should be noted that in some embodiments, any portion of the medical monitoring device (e.g., the lead set 13, the electronics module 11, etc.) may include the adhesive member 96. For example, the body of the medical monitoring device 10 may include the adhesive member 96. Furthermore, in some embodiments, the adhesive member 96 is used to couple certain components of the medical monitoring device 10 to each other. For example, in some embodiments, the adhesive member 96 may facilitate coupling of the electrodes 25 to the lead set 13.

Figure 26:
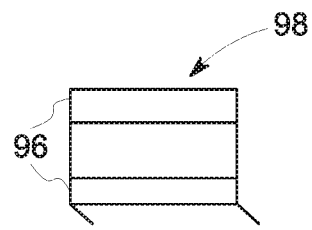
FIG. 26 is a top schematic view of an embodiment of the adhesive member of FIG. 9, in accordance with aspects of the present disclosure.
Figure 27:
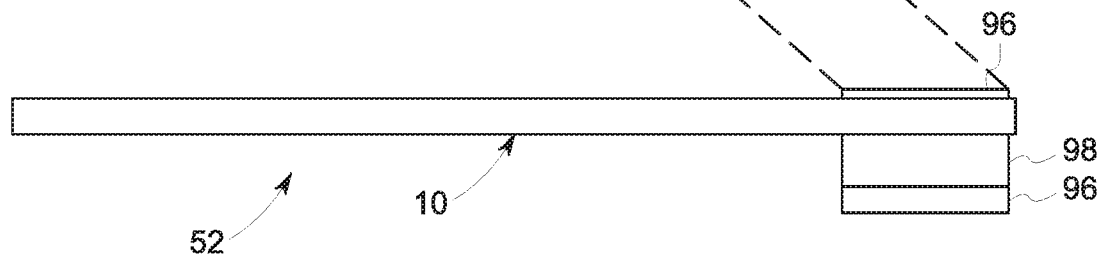
FIG. 27 is a top schematic view of an embodiment of the adhesive member of FIG. 9 employed on the adjustable member, in accordance with aspects of the present disclosure.

FIG. 26-27 include a top schematic view of an embodiment of the adhesive member 96 of FIG. 9, in accordance with aspects of the present disclosure. In the illustrated embodiment, the adhesive member 96 is employed on the adjustable member 52. Specifically, in the illustrated embodiment, two adhesive members 96 are positioned on an adjustment patch 98, such that the two adhesive members 96 may be selectively fixed to one another. In some instances, the adjustment patches 98 may be Velcro™. The adjustment patch 98 may enable the adjustment of the length of electrodes 25. Furthermore, the adjustment patch 98 may be folded, such that the two adhesive members 96 become fixed to one another after coming in contact with one another. In some embodiments, the adhesive member 96 may be omitted from the folded area of the adjustment patch 98. The adjustment patch 98 may be positioned on any suitable location on the medical monitoring device 10. The adhesive member 96 and the adjustment patch 98 may be used to adjust the length of the electrodes 25 and keep slack material from interfering with the patient's mobility or caregiver access.

Figure 28:
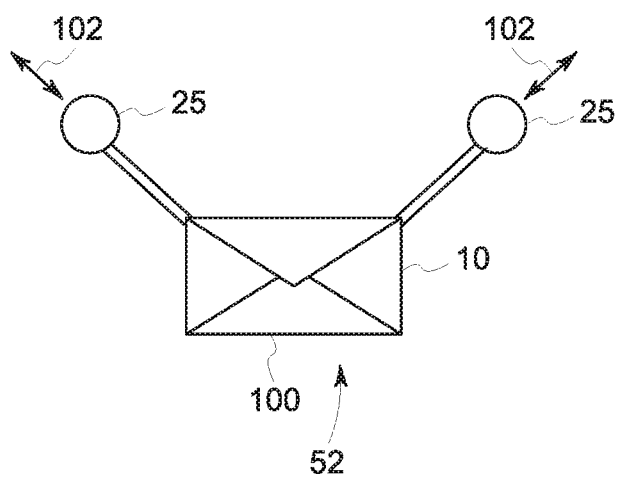
FIG. 28 is a schematic diagram of an embodiment of a storage compartment that holds the medical monitoring device of FIG. 1, in accordance with aspects of the present disclosure.

FIG. 28 is a schematic diagram of an embodiment of a storage compartment 100 that holds the medical monitoring device 10 of FIG. 1, in accordance with aspects of the present disclosure. The storage compartment 100 may hold the medical monitoring device 10. In some embodiments, the storage compartment 100 may hold a portion of the medical monitoring device 10, such as the lead set 13. In the illustrated embodiment, the storage compartment 100 is an envelope that holds the medical monitoring device 10. It should be noted that in further embodiments, the storage compartment 100 may be any suitable housing system. Further, the electrodes 25 are positioned outside of the storage compartment and may be pulled along a radially outward direction 102. The storage compartment 100 may be sealed to house the medical monitoring device 10. The storage compartment may not require the lead sets 11 to fold at small angles (e.g., 5°).

Figure 29:
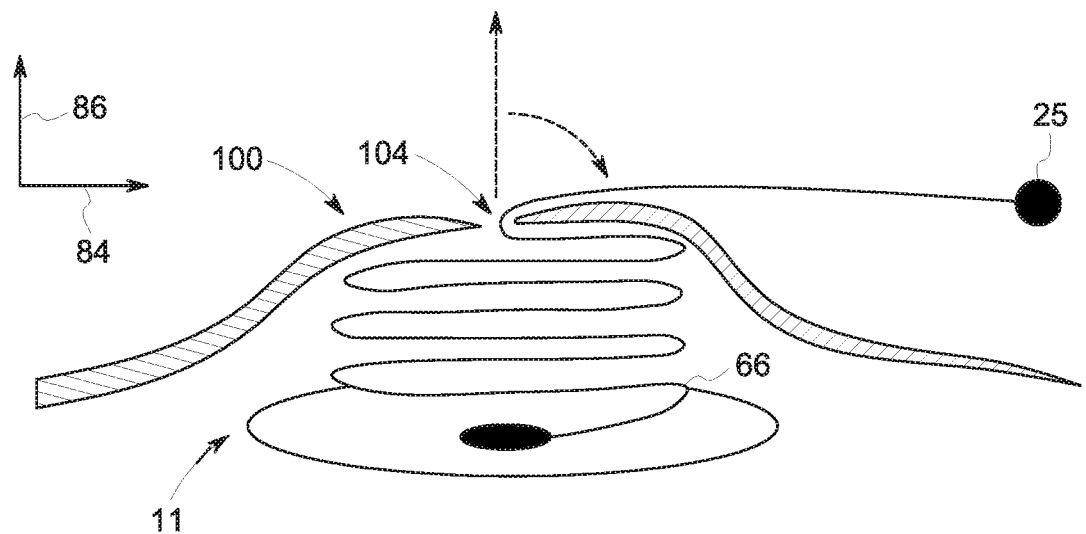
FIG. 29 is a schematic diagram of another embodiment of the storage compartment of FIG. 28, in accordance with aspects of the present disclosure.

FIG. 29 is a schematic diagram of another embodiment of the storage compartment 100 of FIG. 28, in accordance with aspects of the present disclosure. In the illustrated embodiment, an opening 104 on the storage compartment 100 may enable the lead set 13 and/or the signal traces 66 to extend out from the opening 104. However, it should be noted that in some embodiments, the storage compartment 100 may include any suitable number of openings 104, from which electrodes 25 and the signal traces 66 may be extended from. In some embodiments, the opening 104 may include a catching member that may secure the signal trace 66 to the opening 104, such that the signal trace is cannot be retracted further. The storage compartment 100 may be an inexpensive storage compartment, such as a tissue box or any other inexpensive item.

Figure 30:
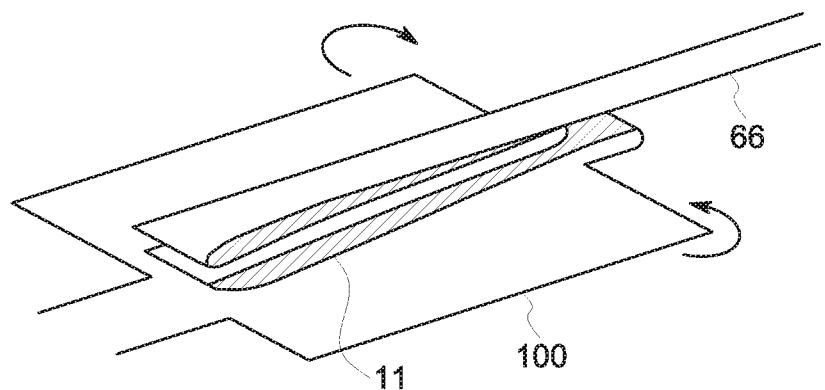
FIG. 30 is a schematic diagram of another embodiment of the storage compartment of FIG. 28, in accordance with aspects of the present disclosure.
Figure 31:
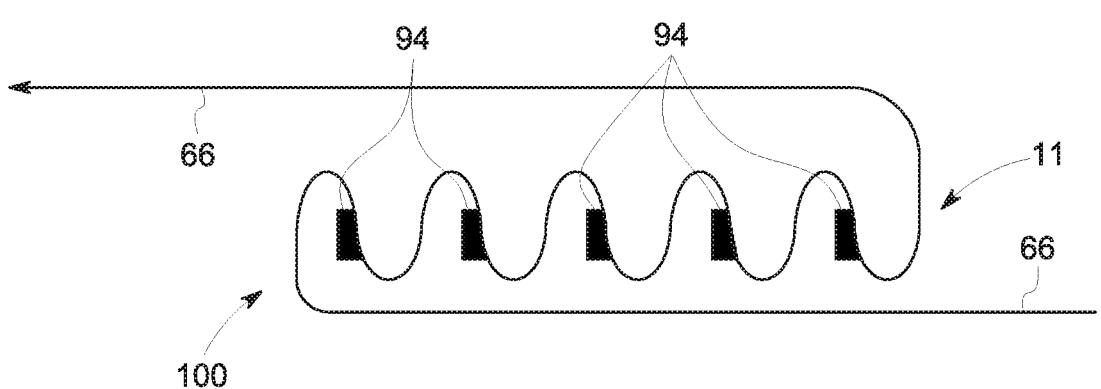
FIG. 31 is a schematic diagram of another embodiment of the storage compartment of FIG. 28, in accordance with aspects of the present disclosure.
Figure 32:
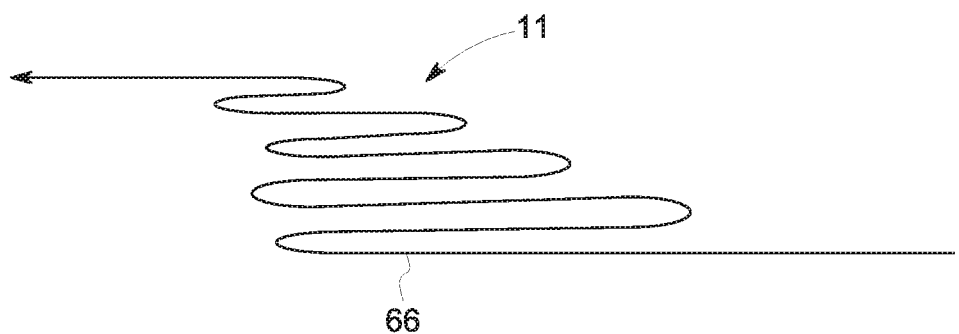
FIG. 32 is a schematic diagram of another embodiment of the storage compartment of FIG. 28t, in accordance with aspects of the present disclosure.

FIG. 30 is a schematic diagram of another embodiment of the storage compartment 100 of FIG. 28, in accordance with aspects of the present disclosure. In the illustrated embodiment, the storage compartment 100 may be rolled around signal traces 66, which have been folded, to create a tube-like housing around the medical monitoring device 10 or any portion of the medical monitoring device 10 (e.g., the lead set 13, the electronics module 11, etc.). As mentioned above, the electronics module 11 (e.g., the signal traces 66, the electrodes 25, etc.) may be printed on a substrate, which may enable the medical monitoring device to fold within the storage compartment. In other embodiments, the electronics module 11 may be adhered to or otherwise applied to a substrate. The electronic module 11 may be formed within a housing in one embodiment. Other designs for the storage compartment 100 are illustrated in FIGS. 31 and 32. FIG. 31 is a schematic diagram of another embodiment of an alternative to the storage compartment 100 of FIG. 28, and FIG. 32 is a schematic diagram of another embodiment of an alternative to the storage compartment 100 of FIG. 28, in accordance with aspects of the present disclosure. Specifically, as illustrated in FIG. 31, the storage compartment 100 may include various adhesive members 96 positioned (or applied) on folds to secure the signal traces 66 to one another, keeping the signal traces in a controlled area. In some embodiments, the adhesive member 96 may also be used to attach the medical monitoring device 10 to the skin of a patient. Furthermore, as illustrated in FIG. 32, the storage compartment may be omitted such that the signal traces 66 may be folded to occupy a smaller area, in some instances, making the medical monitoring device 10 more portable.

It may be beneficial for the components of the medical monitoring device 10 to be insulated against defibrillation pulses, such that the insulation enables the components of the lead set 13 and the electronics module 11 to withstand 5000V peak voltages resulting from a voltage pulse, such as a defibrillation pulse. The components of the medical monitoring device 10 may be insulated by printing the dielectric insulator materials on top of the conductive signal traces 66 or by applying a second surface on top of the signal trace. In some instances, second surface may be achieved by folding or rolling the substrate over the conductive trace to create the second surface.

Figure 33:
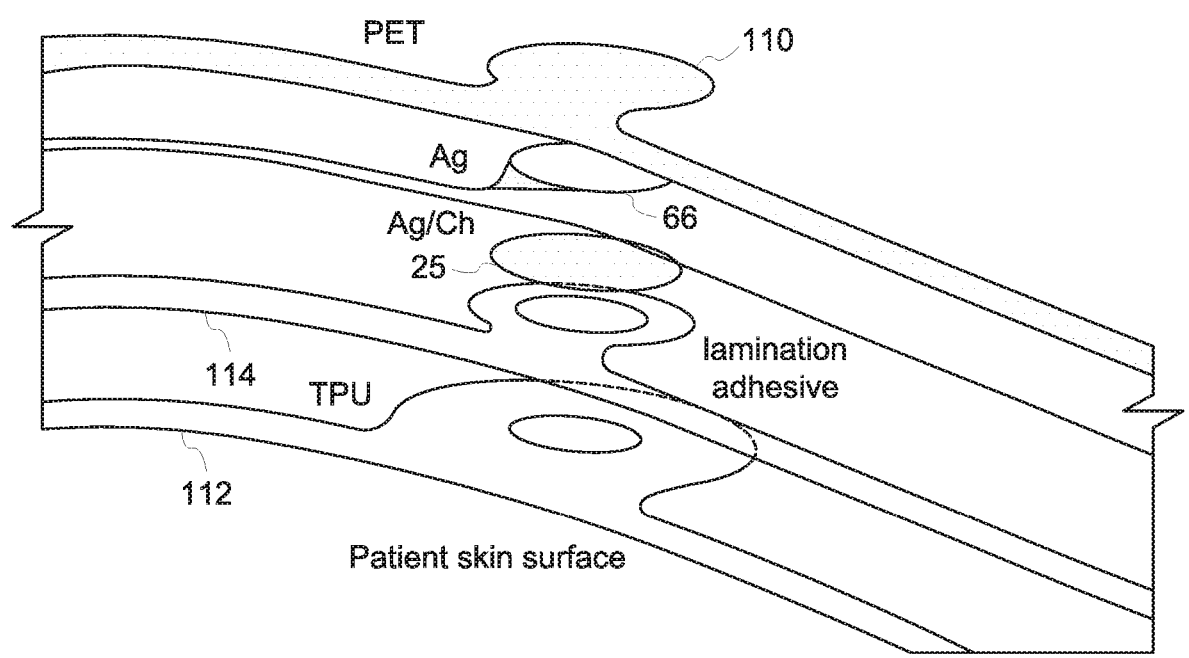
FIG. 33 is a schematic diagram of an embodiment of a printed polyethylene terephthalate (PET) substrate laminated with the thermoplastic polyurethane (TPU) substrate, employed in the medical monitoring device of FIG. 1, in accordance with aspects of the present disclosure.

FIG. 33 is a schematic diagram of a printed PET substrate 110 (e.g., a first substrate layer) laminated with the TPU substrate 112 (e.g., a second substrate layer), in accordance with aspects of the present disclosure. As provided herein, in some embodiments, the components of the medical monitoring device 10 may be printed on a TPU substrate 112. In some instances, printed electronics are printed on a PET substrate 110 because PET is generally convenient to handle in a printing processes, may withstand relatively high temperatures, and does not absorb moisture nor stretch. However, due to the stiff and sharp edges of PET substrates 110, a medical monitoring device 10 intended to be worn on the skin may be uncomfortable and/or give rise to medical anomalies on the skin. In some instances, PET includes unfavorable triboelectric properties and may experience EMI on the ECG, which may not be optimal for ECG applications. Conversely, the TPU substrate 112 is a more flexible and softer material to employ in conjunction or instead of the PET substrate 110. During the printing process, the TPU substrate 112 may not withstand the high temperatures that the PET substrate 110 may withstand. In addition, TPU substrate 112 may be best if handled with stiffening carriers that enable the TPU to maintain its planar structure during the printing process. TPU is comfortable on the skin surface, conforms with body shapes easily, and includes much better triboelectric properties for ECG applications. The TPU is generally stretchable. Indeed, the printing of passive components on flexible substrates may result in a printed lead that increases patient comfort while reducing manufacturing costs.

In some embodiments, the PET substrates 110 are used for printing the conductive signal traces 66 (e.g., using silver ink) and the active electrodes 25 (e.g., using silver ink, silver chloride ink, etc.). In the illustrated embodiment, the signal traces 66 are composed of silver and the electrode 25 is composed of silver/silver-chloride (Ag/AgCl). Furthermore, a laminated adhesive layer 114 may be applied over the signal traces 66 and the electrode 25 to enable the attachment of the TPU substrate 112. In the illustrated embodiment, the TPU substrate 112 may provide the PET lead set 130 with insulation from defibrillation pulses (e.g., 5000V). In some embodiments, the TPU substrate 112 is worn on the skin side for comfortability and convenience. Furthermore, the TPU substrate 112 may protect the skin against the sharp edges of the PET substrate. Additionally, the TPU substrate 112 may reduce the triboelectric interference caused on the ECG by the PET substrate.

It should be noted that additional protective layers may also be employed. For example, typical ECG signal traces are coaxial structures with a conductive layer shielding the signal traces from external electric fields (e.g., EMI). In such cases, there may be different coupling mechanisms contributing to the EMI. The coupling mechanisms may be radio frequency (RF) interference, electrostatic discharges (e.g., EMI) near the electrodes, electrostatic discharges (e.g., EMI) to the signal trace, and mains interference and static electrical charges. In some instances, the coaxial lead wire structures provide protection against these coupling mechanisms. Further, it should be understood that, as provided herein, a layer may include two or more sublayers.

However, implementing coaxial structures on the printed electrodes 25 and signal traces 66 may be difficult. A shielding layer may be printed on both sides of the signal traces 66 to approximate the shielding/insulating of the coaxial structure. Furthermore, in some embodiments, the width of the ground layer of the shielding layer may be approximated. Further, it may be beneficial to protect the components of the medical monitoring device 10 against defibrillation pulses in applications employing electrodes 25 with large areas, such as in ECG applications. As mentioned above, protecting the components of the medical monitoring device 10 may be designed to withstand up to a 5 kV defibrillation pulse. In some embodiments, the insulation of the components of the medical monitoring device may be positioned between the shielding layer and the signal trace 66 and may withstand the 5 kV defibrillation pulse. Printing the insulation in between the shielding layers and signal trace 66 may be difficult. In some embodiments, the shielding layer (e.g., the TPU substrate 112) is laminated or glued, for example, using the lamination adhesive 114 to laminate or glue the structure together from multiple polymer layers. However, laminating or gluing the shielding layer as described above may be expensive to manufacture and may result in a stiff component not capable of bending.

Figure 34:
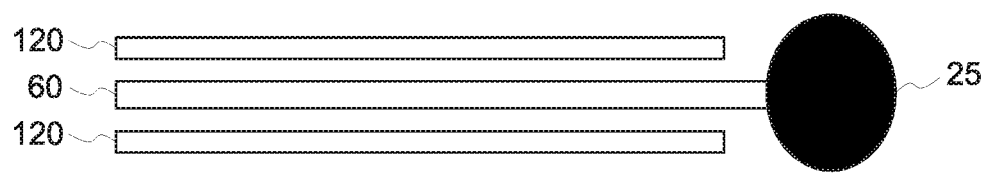
FIG. 34 is a schematic diagram of an embodiment of a planar shielding layer printed on the same substrate on which signal traces of the medical monitoring device of FIG. 1 are printed onto, in accordance with aspects of the present disclosure.

Printing planar shielding layers over the signal traces 66 and on the same substrate with signal traces 66 may provide an alternative to traditional shielding techniques. FIG. 34 is a schematic diagram of a planar shielding layer 120 (e.g., the third substrate layer) printed on the same substrate on which the signal traces 66 of the medical monitoring device 10 of FIG. 1 are printed onto, in accordance with aspects of the present disclosure.

In the illustrated embodiment, two polymer layers are used as the shielding layer 120. In some embodiments, using two polymer layer maintains the flexibility of the medical monitoring device 10. The electrical shield properties of interest include the following.

First, with regard to RF interference, the coupling of the RF interference is marginally reduced. However, adequate attenuation may be achieved by adding passive filtering to the amplifier input. Second, with regard to mains interference and interference from statically charged objects, the mains interference and other interferences may capacitively couple to the signal traces 66. In some instances, the grounded shielding layer 120 modify the electric fields so that the coupling from a distant source is attenuated significantly. For example, in a geometry with two millimeter (mm) wide traces with 4 mm spacing, the coupling may be reduced by a factor of six. Third, with regard to the electrostatic discharges, the electrostatic discharges in the vicinity may also capacitively couple and behave as described above. If the electrostatic discharge happens close to the signal traces 66, the attenuation factor may smaller. Fourth, with regard to direct discharges, the probability of direct discharges to the signal traces 66 is reduced because the shielding layer 120 provide a low-impedance path for the discharge.

Figure 35:
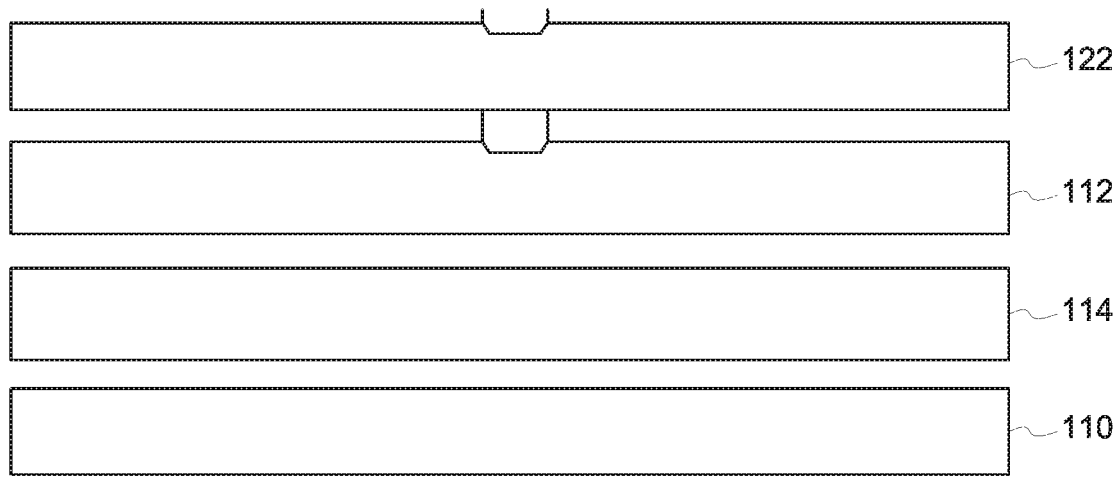
FIG. 35 is a schematic diagram of an embodiment of the signal traces of the medical monitoring device of FIG. 1, whereby the signal traces are sprayed with shielding material, in accordance with aspects of the present disclosure.

In some embodiments, the components (e.g., signal traces 66, electrodes 25, etc.) of the medical monitoring device 10 may be shielded using other systems and methods. FIG. 35 is a schematic diagram of an embodiment of the signal traces of the medical monitoring device of FIG. 1, whereby the signal traces are sprayed with shielding material, in accordance with aspects of the present disclosure. For example, in the illustrated embodiment, a shielding layer 120 may be formed by spraying a conductive shielding material 122. In some embodiments, the shielding layer 120 may be included in addition to or alternatively to the shielding layer 120. Alternatively or additionally, flexible metamaterial RF filters may be printed to filter out unwanted signals. Alternatively or additionally, poly(3,4-ethylenedioxythiophene) (PEDOT: PSS) or other intrinsically conducting polymers for shielding may be used as the shielding layer 120, such that metal films shield by reflection and conducting polymers shield by absorption (e.g., "stealth technology"). Alternatively or additionally, the conductor (e.g., the signal trace 66 or the electrode 25) may be positioned between 2 layers of conductive shielding film (e.g. PEDOT), for example, using pressure-sensitive adhesive. Alternatively, commercial PEDOT-coated films, such as those employed on touchscreen displays, may be used as substrates for printing the shielding layers 120. Alternatively or additionally, two-dimensional (2D) transition metal carbides (e.g., nano-materials) in very thin layers may be used. These 2D transition metal carbides may be spray-coated to achieve the shielding efficiency of copper.

In some embodiments, the conductive shielding layer 120 may be printed on both sides of the signal trace 66. This may be beneficial in many applications, especially in ECG applications, in which a defibrillation-proof ECG system is not allowed to draw more than 10% of the defibrillation pulse energy (e.g., 10% of a 5 kV defibrillation pulse). As discussed herein, in some embodiments, the insulation may be omitted, and the embodiments described herein may lead to a more economical and user friendly construction of an ECG.

In a typical construction, there is a high voltage resistor in each ECG input in series with each signal trace 66. When a defibrillation pulse is applied between two electrodes 25, this high voltage resistor provides sufficiently high impedance so that the energy drawn from the defibrillation pulse remains within allowed limits. In typical designs, all shielding layers are connected to electronic grounds, which may require insulation between the shielding layer and each signal trace when the 5 kV defibrillation pulse is applied between two electrodes. Absent the insulation between the shielding layer and the signal trace, the defibrillation pulse may result in unwanted functionality, such as a short circuit through the shielding layer.

To facilitate preventing this short circuit, the embodiments disclosed herein include methods for printing a shielding layer 120 over each signal trace 66. The shielding layers 120 of each signal trace 66 may be connected together. Each shielding layer may be connected to an electronics ground through the high voltage resistor. In some embodiments, the high voltage resistor is printed via the same process used to print the signal traces 66 and shielding layer 120. If the voltage of the defibrillation pulse travels from the signal trace 66 to the shielding layer 120, the high voltage resistor may limit the current to a suitable magnitude. Resistors in series with the shielding layers 120 may reduce the attenuation against external interference. In some instances, the coupling impedance is sufficient to attenuate the interference, for example, for a 100 kΩ high voltage resistor. In some embodiments, the resistor has been dimensioned so that it may break because of the energy from the defibrillation pulse. Because of the large dimensions of the resistor, there the resistor may be less likely to arc over, which may prevent the drawing of excessive energy from the defibrillation pulse.

One aspect of the invention is to enhance signal display recovery after defibrillation pulses experienced by the medical monitoring device 10. It may be unwanted for an electrical breakdown between the signal trace 66 and shielding layer 120 to occur because a conductive path may result. During the electrical breakdown, the input impedance may be reduced since the shield grounding resistor may appear as an additional load in the input. Three solutions to this are described.

First, back-to-back diodes from signal trace 66 to shielding layer 120 may prevent an uncontrolled breakdown of the insulator. The diodes may be discrete components, but in some embodiments, the diodes may be printed. In some embodiments, the diodes may be printed such that they provide low enough leakage current.

Second, a printed spark gap between the signal trace 66 and shielding layer 120 may provide a controlled path for electrical breakdown. The spark gap must be designed so that it does not create a short circuit due to arcing over the resistor.

Third, the signal trace 66 may be designed such that the signal trace 66 shorts with the shielding layer 120, but the grounding resistor may be designed such that it breaks open with the defibrillation pulse. In some instances, breaking of the resistor makes the medical monitoring device more sensitive to external interference, but does not make the medical monitoring device inoperable.

Figure 36:
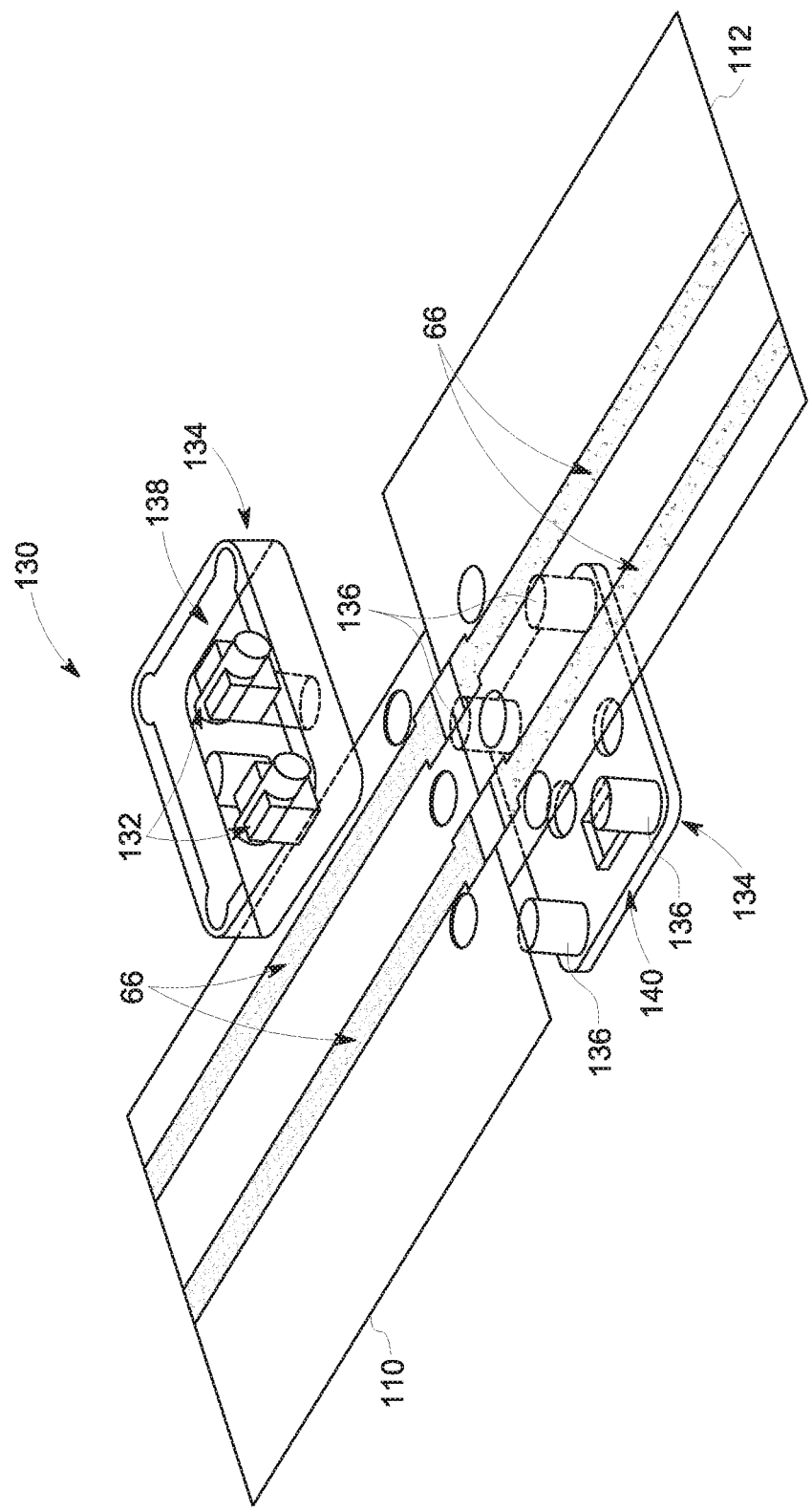
FIG. 36 is a schematic diagram of an embodiment of a resistor carrier employed in the medical monitoring device of FIG. 1, in accordance with aspects of the present disclosure.

FIG. 36 is an embodiment of a resistor carrier 130 employed in the medical monitoring device 10 of FIG. 1, in accordance with aspects of the present disclosure. In some embodiments, the lead set 13 of the medical monitoring device 10 may include a resistor carrier 130. In some embodiments, the medical monitoring device 10 may be protected from defibrillation pulses by using discrete metal electrode leadless face (MELF) resistors 132 (e.g., cylindrical in shape) of a suitable resistance (e.g., 50 kΩ). The MELF resistors 132 may be integrated directly onto the flexible substrate (e.g., TPU substrate 112). However, it should be noted that in some embodiments, the MELF resistors may be integrated by connecting two different substrates. For example, if the lead set 13 is made from TPU and the main electronics 13 of the medical monitoring device 10 (e.g., MCU, communications, ECG, etc.) are integrated onto the PET substrate 110, as described above, the two substrates may be joined.

Further, in some instances, it may be beneficial for the MELF resistors 132 to not interact the environment during defibrillation. In some embodiments, a suitable dielectric gap, for example, of 4 mm, in all directions from the high voltage lead may prevent the MELF resistor 132 from interacting with the environment. The dielectric gap may be an air-gap. Alternatively, a thickness of 4 mm in all directions may be employed by the MELF resistors to create the dielectric gap of suitable dimension. It should be noted that in some embodiments, the dielectric gap may be more or less than the 4 mm dielectric gap discussed above.

Figure 37:
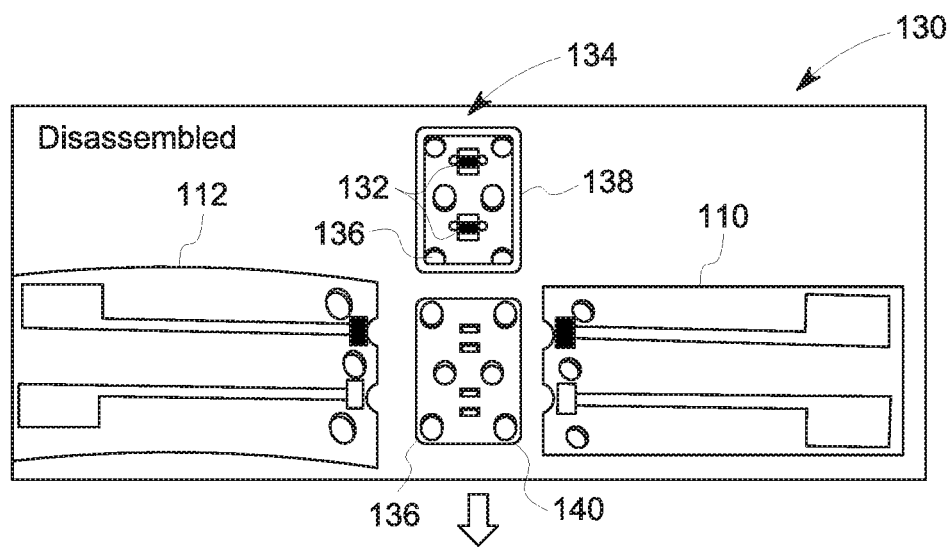
FIG. 37 is a schematic diagram of an embodiment of the resistor carrier of FIG. 36 in an unassembled state, in accordance with aspects of the present disclosure.
Figure 38:
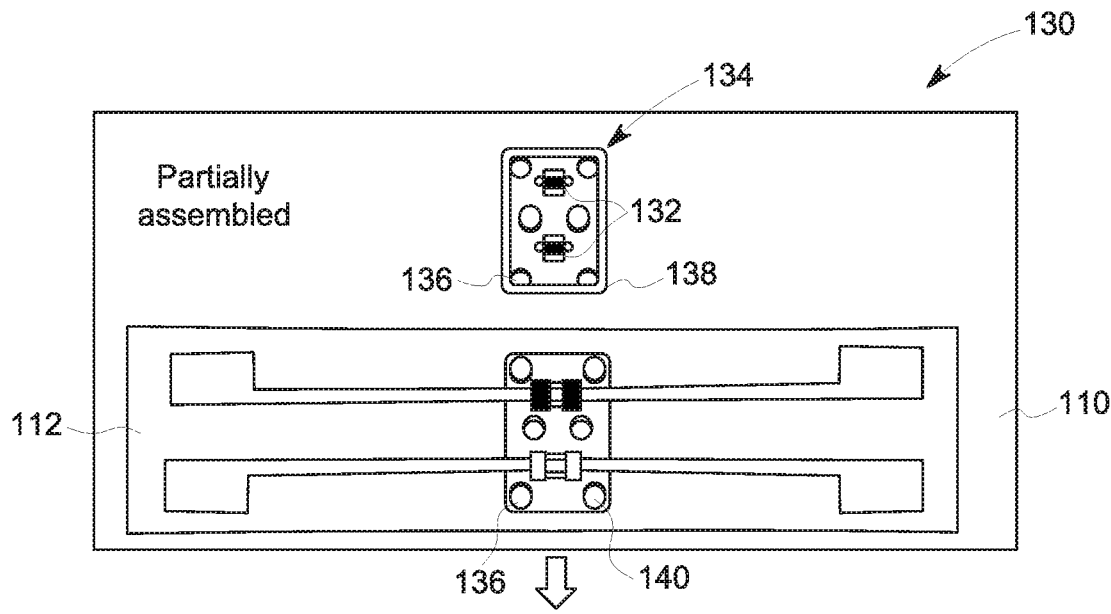
FIG. 38 is a schematic diagram of an embodiment of the resistor carrier of FIG. 36 in a partially assembled state, in accordance with aspects of the present disclosure.
Figure 39:
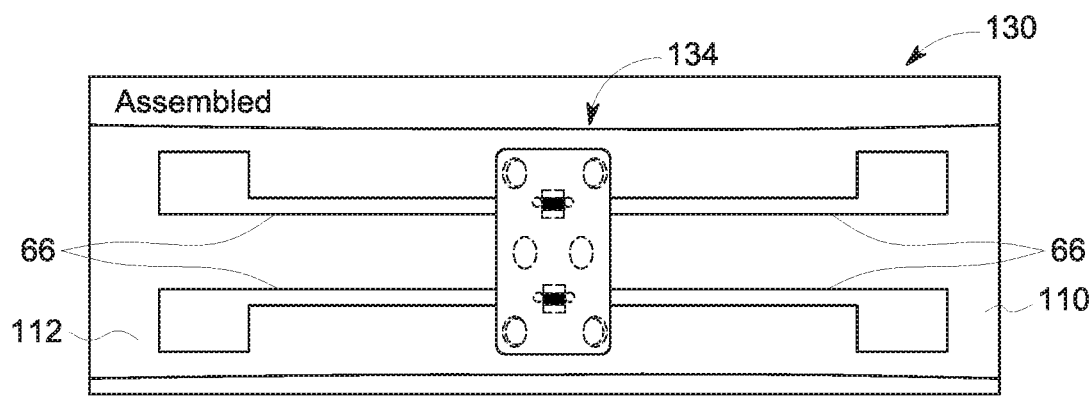
FIG. 39 is a schematic diagram of an embodiment of the resistor carrier of FIG. 36 in an assembled state, in accordance with aspects of the present disclosure.

The resistor carrier 130 may hold the MELF resistors 132 in place and align the MELF resistors 132 for attachment to the substrates (e.g., the PET substrate 110, the TPU substrate 112, etc.). Additionally, the resistor carrier 130 may provide the suitable a sufficient dielectric gap. In addition, the resistor carrier 130 may align the substrates (e.g., PET substrate 110, the TPU substrate 112) for attachment to the MELF resistors 132. In some embodiments, the resistor carrier 130 mechanically couples the first substrate (e.g., the PET substrate 110) and the second substrate (e.g., the TPU substrate 112) to each other. In the illustrated embodiment, the MELF resistors 132 are held in place by a fixture mechanism 134. The fixture mechanism 134 includes pins 136 on a top case 138, a bottom case 140, or a combination thereof. In some embodiments, the pins 136 mate the top case 138 and the bottom case 140. Further, the pins 136 may engage the substrates, such that they mate with the top case 138 and the bottom case 140. As such, in the illustrated embodiment, the first substrate (e.g., the PET substrate 110) and the second substrate (e.g., the TPU substrate 112) are be fixed in between the top case 138 and the bottom case 140. To enhance the conductivity of the resistor and/or the signal traces 66 (e.g., the conductor connections), certain adhesives such as conductive epoxy or conductive PSA, among others, may be used. The process of assembling the resistor carrier 130 is depicted in FIGS. 37-39. Specifically, FIGS. 37-39 depict a schematic diagram of an embodiment of the resistor carrier of FIG. 36 in an unassembled state, in a partially assembled state, and in an assembled state, respectively.

Figure 40:
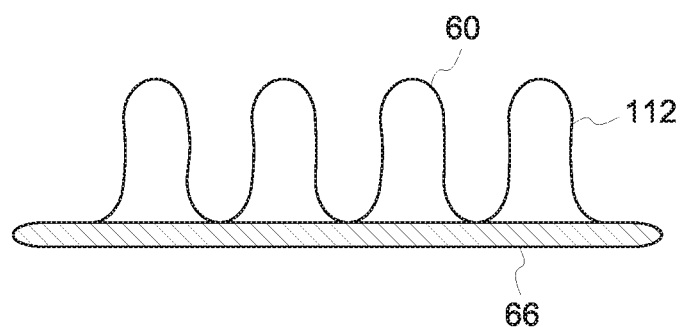
FIG. 40 is a schematic diagram of an embodiment of the substrate of FIG. 8 employing stretchable ink, in accordance with aspects of the present disclosure.
Figure 41:
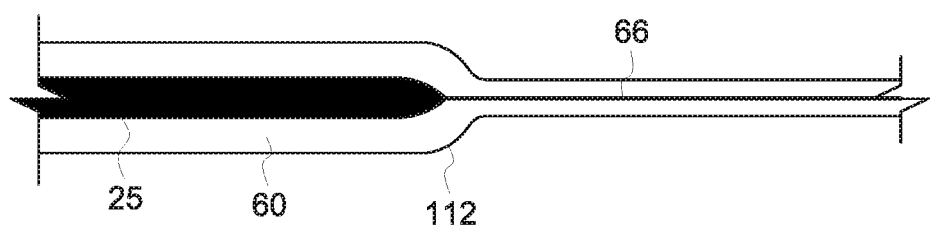
FIG. 41 is a schematic diagram of another embodiment of the substrate of FIG. 8 employing the stretchable ink of FIG. 40, in accordance with aspects of the present disclosure.

FIGS. 40 and 41 are a schematic diagrams of respective embodiments of the substrate of FIG. 8 employing stretchable ink 150, in accordance with aspects of the present disclosure. Although the TPU substrate 112 is stretchable, in typical designs, the printed traces may not be as flexible. As a result, during moderate to extreme mechanical deformations, the conductor traces may unwind or detach. To alleviate this, the embodiments disclosed herein include using stretchable inks 150 to print the signal traces 66, the electrodes 25, and/or other components of the medical monitoring device onto the substrate 60. In some embodiments, the stretchable inks 150 may also deform and enable folding. In some embodiments, the stretchable inks 150 may include materials that are magnetic and self-sealing. Alternatively or additionally, the stretchable inks 150 may include materials that are gel or liquid.

Figure 42:
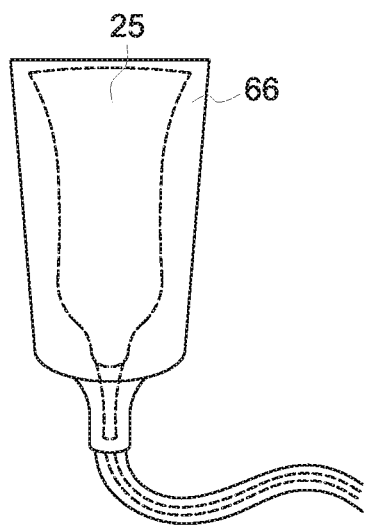
FIG. 42 is a schematic diagram of an embodiment of the substrate of FIG. 8 employing the stretchable ink of FIG. 40, which is printed while the substrate of FIG. 8 is in use, in accordance with aspects of the present disclosure.
Figure 43:
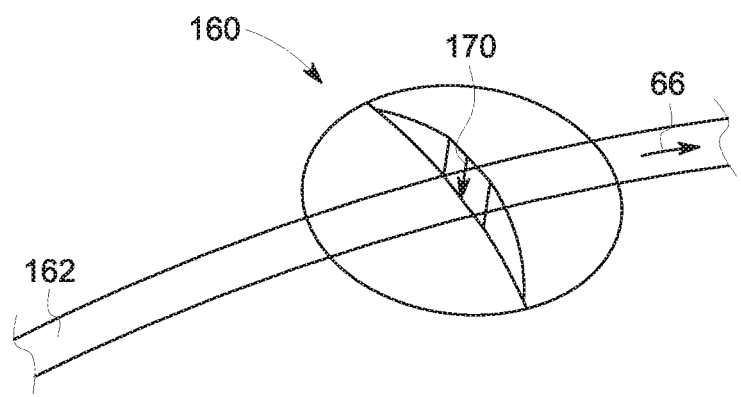
FIG. 43 is a schematic diagram of an embodiment a portable printing device, in accordance with aspects of the present disclosure.
Figure 44:
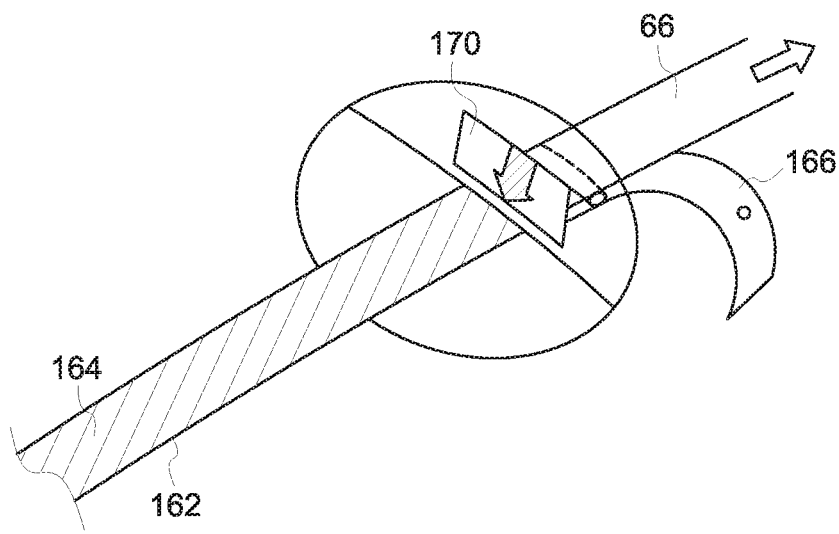
FIG. 44 is a schematic diagram of another embodiment of the portable printing device of FIG. 43, in accordance with aspects of the present disclosure.
Figure 45:
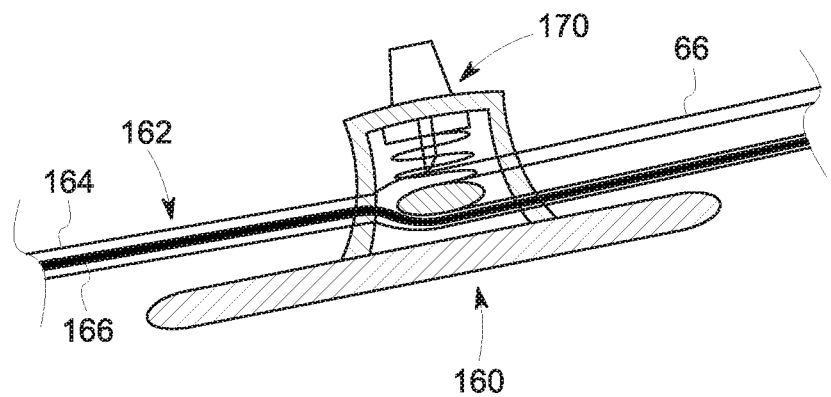
FIG. 45 is a schematic diagram of another embodiment of the portable printing device of FIG. 43, in accordance with aspects of the present disclosure.
Figure 46:
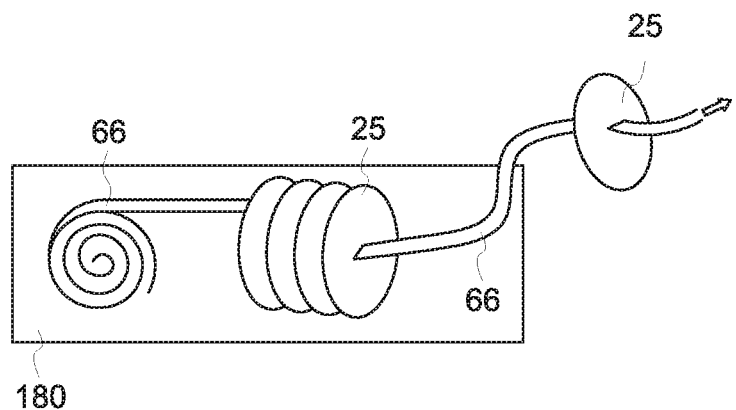
FIG. 46 is a schematic diagram of another embodiment of the portable printing device of FIG. 43, in accordance with aspects of the present disclosure.

FIG. 42 is a schematic diagram of an embodiment of the substrate 60 of FIG. 8 employing the stretchable ink 150 of FIGS. 40-41 that is printed while the substrate 60 of FIG. 8 is in use, in accordance with aspects of the present disclosure. The substrate 60 may be in use when worn by a patient. In some embodiments, the signal traces 66, the electrodes 25, and other components of the medical monitoring device 10 may be printed while the medical monitoring device 10 is worn on the person. In some embodiments, using conductive and dielectric gels may facilitate printing while the medical monitoring device 10 is worn. For example, the conductive and dielectric gels may be applied to the substrate, and the conductive and dielectric gels may harden after a suitable period of time.

The use of soft flexible materials opens new areas for manufacturing and assembly of electronic devices on the lead-set. Traditional methods include solders, epoxies and glues that are flexible during their initial application, and then harden to rigidly lock the components together. Alternatively, the use of soft, flexible materials enables the use of mechanical fasteners, such as staples applied to paper, crimps as applied cables, etc. The flexibility of the substrates used herein offers several features that do not require holes to generate fixtures, which may also not require the mechanical fasteners to penetrate the substrates. Furthermore, the compression of the substrates exerts force back upon the fastener ensuring contact. The mechanical fastener may be applied by itself (e.g. a rivet machine) or be integrated into a device (e.g. chip with crimp leads). In some embodiments, the pick-and-place machine may position and attach the substrate. These methods of assembly eliminate the need for high-temperature reflow (e.g., solder) or for curing processes (e.g., epoxy).

In some embodiments, the crimp may be integrated into the chip package to enable modifying the pick-and-place to attach during placement. Another concept is to use the soft materials as the fasteners themselves, e.g. via slots configured to hold corners or tabs of the substrate, such that lamination may not be required. The concept relies on the substrate material being flexible but retaining some opposing force. Alternatively, the integration may be enhanced with adhesives that do not cure (for example adhesive tape) or with shape-memory devices (paper clip). This concept could be extended to new geometries for electrical connection (especially multiple connections and layer crossovers) and machines to bend/insert/assemble.

FIG. 43-46 depict respective schematic diagrams of an embodiment a portable printing device 160, in accordance with aspects of the present disclosure. In the illustrated embodiments, a tape roll (e.g., a Microtape Roll) is rolled into a small cylinder (not shown). The tape 162 of the tape roll may have an adhesive liner 164 on one side and a release liner 166 on the other side. Further, in the illustrated embodiment, the portable printing device includes a guillotine 170 that may allow cutting of the tape 162 at the desired length. In some embodiments, the attachment methods described above for connecting the lead-set and the electronic module may be facilitated using the printing device 160.

The portable printing device 160 includes a package 180 that may receive the signal trace 66 and the electrodes 25. In some embodiments, the electrodes may include openings that enable the electrodes 25 to engage with the signal traces 66. In some embodiments, the signal traces 66 may slide into the opening of the electrodes 25. After the electrodes are arranged at suitable positions on the package 180, the signal trace 66 may be cut to the target length using any suitable cutting method. As such, the electronic module may be assembled manually.

In this case, a separate device may be provided which includes the signal trace 66 in a roll. In some embodiments, the signal trace 66 may easily peel off certain amounts of dielectric and create a conductive spot for crimping or snapping of electrodes 25 after they slide into the signal trace. Accordingly, if the conductor is a discrete trace, a certain amount of dielectric may peel off to create a conductive spot for crimping or snapping of electrodes 25.

Technical effects of the invention include a disposable, conformable, and high performing medical monitoring device with sensing capabilities that can be adjusted to different body shapes and sizes. The disposable and adjustable vital sign monitoring device may include an electronics module and, in certain embodiments, a flexible adjustable lead-set. In some embodiments, the electronics module may include a shielding component that protects certain aspects of the electronics module. Furthermore, the flexible adjustable lead set may provide patient comfort and care-giver workflow benefits. In some embodiments, the medical monitoring device may be disposable, such that the medical monitoring device may be used by one patient and disposed of after use. In some embodiments, certain components of the electronics module are printed on a first substrate layer. A second substrate layer may be applied (e.g., printed) over the first substrate layer to insulate certain components of the electronics module. A third substrate layer may be applied (e.g., printed) over the first and/or second substrate layer to shield the certain components of the electronics module from certain EMI.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for monitoring medical conditions, the system comprising:
   a conformable medical monitoring device, comprising:
      a first substrate layer, wherein the first substrate layer is conductive and comprises an electronics module, a plurality of signal traces and at least one electrode, wherein one or more of the plurality of signal traces electrically couple the at least one electrode to the electronics module, and wherein the one or more of the plurality of signal traces is in a spiral arrangement that is to unwind when the one or more of the plurality of signal traces is extended along a lateral axis;
      a second substrate layer positioned over the electronics module, the first substrate layer, or any combination thereof, wherein the second substrate layer is configured to insulate the electronics module, the first substrate layer, or any combination thereof, and wherein at least two back-to-back diodes provide a low leakage current between the one or more signal traces and a third substrate layer to prevent a breakdown of the second substrate layer in response to a defibrillation pulse;
      the third substrate layer positioned over the second substrate layer, wherein the third substrate layer is configured to reduce electromagnetic interference, wherein the third substrate layer is conductive; and
      an adjustable system coupled to the first substrate layer, wherein the adjustable system is configured to change a position of the at least one electrode relative to the electronics module.

2. The system of claim 1, wherein the adjustable system is configured to move from a first configuration to a second configuration to change the position of the at least one electrode relative to the electronics module.

3. The system of claim 1, wherein changing the position comprises changing between a folded configuration and an unfolded configuration of the plurality of signal traces.

4. The system of claim 1, wherein the electronics module comprises one or more LED lights, one or more sensors, one or more thermistors, one or more transceivers, or any combination thereof.

5. The system of claim 4, wherein a laminated adhesive layer is configured to facilitate attachment of the second substrate layer to the first substrate layer, facilitate attachment of third substrate layer to the second substrate layer, or any combination thereof.

6. The system of claim 1, wherein the first substrate layer is a polyethylene terephthalate (PET) substrate and the second substrate layer is a thermoplastic polyurethane (TPU) substrate and wherein the third substrate layer comprises a polymer mixture poly(3,4-ethylenedioxythiophene) (PEDOT:PSS).

7. The system of claim 1, wherein one or both of the plurality of signal traces and the at least one electrode are printed on the first substrate layer.

8. The system of claim 1, wherein a first electrode of the at least one electrode is in electrical communication with an amplifier input, wherein a passive filter is applied to the amplifier input to achieve a target attenuation.

9. The system of claim 1, wherein the third substrate layer is connected to an electronics ground through a resistor, wherein the resistor is configured to limit energy resulting from the voltage pulse to a target limit, wherein the resistor is a metal electrode leadless face (MELF) resistor.

10. The system of claim 1, comprising a plurality of diodes configured to electrically couple the plurality of signal traces to the third substrate layer.

11. The system of claim 1, comprising a printed spark gap positioned between the plurality of signal traces and the third substrate layer to provide a controlled path for electrical breakdown.

12. A method for manufacturing a printed lead set with an electronics module for use in a medical monitoring device, wherein the method comprises:
   printing a plurality of conductive signal traces and a plurality of electrodes on a first conformable substrate layer, wherein the first conformable substrate layer is conductive;
   printing a second shielding substrate layer over the first conformable substrate layer, the plurality of conductive signal traces, the plurality of electrodes, or any combination thereof, wherein at least one of the plurality of conductive signal traces is in a spiral arrangement that is to unwind when the at least one of the plurality of conductive signal traces is extended along a lateral axis, wherein at least two back-to-back diodes provide a low leakage current between the plurality of conductive signal traces and a third shielding substrate layer to prevent a breakdown of the second shielding substrate layer in response to a defibrillation pulse; and
   applying the third shielding substrate layer over the second shielding substrate layer, wherein the third shielding substrate layer is configured to shield the first conformable substrate layer, the second shielding substrate layer, the plurality of conductive signal traces, the plurality of electrodes, or any combination thereof from electromagnetic interference, and wherein the third shielding substrate layer is conductive.

13. The method of claim 12, wherein printing the second shielding substrate layer comprises using stiffening carriers configured to maintain the second shielding substrate layer in a planar configuration during the printing.

14. The method of claim 12, further comprising applying one or more additional shielding substrate layers under or over the first conformable substrate layer, the second shielding substrate layer, the third shielding substrate layer, or any combination thereof.

15. The method of claim 12, wherein applying the third shielding substrate layer comprises spraying poly(3,4-ethylenedioxythiophene) over the second shielding substrate layer.

16. The method of claim 12, further comprising printing a plurality of resistors on the first conformable substrate layer, wherein each of the plurality of resistors comprise a dielectric gap positioned a suitable distance away from a high voltage lead.

17. The method of claim 12, wherein printing the second shielding substrate layer comprises printing the second shielding substrate layer on the portions of each of the plurality of signal traces not in contact with the first conformable substrate layer.

18. A conformable medical monitoring device, comprising:
- a first substrate layer, wherein the first substrate layer is conductive and comprises an electronics module, a plurality of signal traces, and at least one electrode, wherein one or more of the plurality of signal traces electrically couple the at least one electrode to the electronics module, and wherein the one or more of the plurality of signal traces is in a spiral arrangement that is to unwind when the one or more of the plurality of signal traces is extended along a lateral axis;
- a second substrate layer positioned over the electronics module, the first substrate layer, or any combination thereof, wherein at least two back-to-back diodes provide a low leakage current between the plurality of signal traces and a third substrate layer to prevent a breakdown of the second substrate layer in response to a defibrillation pulse; and
- a resistor carrier configured to hold at least one resistor in place and fix the second substrate layer to the third substrate layer, wherein the third substrate layer is conductive.

19. The conformable medical monitoring device of claim 18, further comprising one or more shielding substrate layers positioned between the first and second substrate layer, between the second and third substrate layer, or any combination thereof.

20. The conformable medical monitoring device of claim 18, wherein the third substrate layer is positioned over the second substrate layer, wherein the third substrate layer is configured to reduce electromagnetic interference caused by a voltage pulse.

* * * * *